(12) United States Patent
Stolen et al.

(10) Patent No.: US 8,480,662 B2
(45) Date of Patent: Jul. 9, 2013

(54) SYSTEMS AND DEVICES FOR PHOTOABLATION

(75) Inventors: Craig Stolen, New Brighton, MN (US); Joseph M. Pastore, Woodbury, MN (US); Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 709 days.

(21) Appl. No.: 11/895,035

(22) Filed: Aug. 22, 2007

(65) Prior Publication Data

US 2009/0054883 A1     Feb. 26, 2009

(51) Int. Cl.
*A61B 18/18*          (2006.01)

(52) U.S. Cl.
USPC .................................. 606/9; 607/88; 607/89

(58) Field of Classification Search
USPC .......................................... 606/15; 607/88–94
See application file for complete search history.

(56) References Cited

U.S. PATENT DOCUMENTS

| | | |
|---|---|---|
| 4,650,770 A | 3/1987 | Liu et al. |
| 4,686,979 A | 8/1987 | Gruen et al. |
| 5,041,108 A | 8/1991 | Fox |
| 5,188,632 A | 2/1993 | Goldenberg |
| 5,470,307 A | 11/1995 | Lindall |
| 5,484,433 A | 1/1996 | Taylor et al. |
| 5,651,785 A | 7/1997 | Abela et al. |
| 5,776,129 A | 7/1998 | Mersch |
| 5,785,704 A | 7/1998 | Bille et al. |
| 5,824,005 A | 10/1998 | Motamedi et al. |
| 6,143,019 A * | 11/2000 | Motamedi et al. ............... 607/89 |
| 6,176,871 B1 * | 1/2001 | Pathak et al. ................. 623/1.21 |

(Continued)

FOREIGN PATENT DOCUMENTS

| | | |
|---|---|---|
| EP | 1253943 B1 | 9/2008 |
| JP | 10085228 A | 4/1998 |

(Continued)

OTHER PUBLICATIONS

"AuroLase Cancer Therapy", [online]. © 2006 Nanospectra Biosciences, Inc. [retrieved Mar. 20, 2007]. Retrieved from the Internet: <URL: http://www.nanospectra.com/aurolase.htm>, (2006), 2 pgs.

(Continued)

*Primary Examiner* — Bill Thomson
*Assistant Examiner* — Jeffrey Lipitz
(74) *Attorney, Agent, or Firm* — Schwegman Lundberg & Woessner, P.A.

(57) ABSTRACT

The invention provides a catheter for optical ablation of tissue in a living body, the catheter including: a distal end; a proximal end; an elongate catheter body coupled between the distal end and the proximal end; a light emission device at the distal end and configured to emit an ablation light having characteristics selected to regulate an optically regulatable transcription control element operably linked to a nucleic acid sequence for a gene product, the expression of which gene product in cells directly or indirectly kills cells; and a projection control mechanism coupled to the light emission device and configured to control an effectively illuminated area where the optically regulatable transcription control element is effectively regulatable by the ablation light projected from the light emission device. Also provided is a system which includes the catheter, and methods to prevent, inhibit or treat AF which employ an expression cassette and/or one or more selected wavelengths of light.

13 Claims, 8 Drawing Sheets

U.S. PATENT DOCUMENTS

| | | | |
|---|---|---|---|
| 6,572,609 | B1 | 6/2003 | Farr et al. |
| 6,660,001 | B2 | 12/2003 | Gregory |
| 6,733,996 | B2 | 5/2004 | Froehlich et al. |
| 6,858,429 | B2 | 2/2005 | Quail et al. |
| 2002/0198576 | A1* | 12/2002 | Chen et al. ............... 607/88 |
| 2003/0055307 | A1* | 3/2003 | Elmaleh et al. ............ 600/1 |
| 2003/0191459 | A1* | 10/2003 | Ganz et al. ................ 606/15 |
| 2004/0006333 | A1 | 1/2004 | Arnold et al. |
| 2006/0034943 | A1 | 2/2006 | Tuszynski |
| 2006/0253113 | A1 | 11/2006 | Arnold et al. |
| 2007/0060984 | A1* | 3/2007 | Webb et al. ............... 607/89 |
| 2007/0078451 | A1 | 4/2007 | Arnold et al. |
| 2007/0168000 | A1 | 7/2007 | Happawana et al. |

FOREIGN PATENT DOCUMENTS

| | | |
|---|---|---|
| JP | 10155805 | 6/1998 |
| JP | 11511999 | 10/1999 |
| JP | 2003530146 | 10/2003 |
| JP | 2006516465 | 7/2006 |
| WO | WO-92/10142 A1 | 6/1992 |
| WO | WO-97/07735 A1 | 3/1997 |
| WO | WO-9707735 A1 | 3/1997 |
| WO | WO-0158240 A2 | 8/2001 |
| WO | WO-2004069072 A2 | 8/2004 |
| WO | WO-2004/082736 A2 | 9/2004 |
| WO | WO-2009/025826 A1 | 2/2009 |

OTHER PUBLICATIONS

"International Application Serial No. PCT/US2008/009922, International Search Report mailed Nov. 28, 2008", 5 pgs.

"International Application Serial No. PCT/US2008/009922, Written Opinion mailed Nov. 28, 2008", 9 pgs.

Adams, S. R., et al., "Controlling cell chemistry with caged compounds", *Ann. Rev. Physiol.*, 55, (1993), 755-784.

Curley, K., et al., "Light-activated proteins", *Current Opinion in Chemical Biology*, 3, (1999), 84-88.

Dachs, G. U., et al., "From bench to bedside for gene-directed enzyme prodrug therapy of cancer", *Anti-Cancer Drugs*, 16(4), (2005), 349-359.

Kizana, E., et al., "Fibroblasts modulate cardiomyocyte excitability: implications for cardiac gene therapy", *Gene Therapy*, 13, (2006), 1611-1615.

Koch, M., et al., "Gene Therapeutic Prevention of Atrioventricular Conduction Delay in Pigs with Persistent Atrial Fibrillation and Heart Failure", *Circulation*, 114(II), (Abstract No. 740), (2006), p. 127.

Spencer, D M, "Developments in suicide genes for preclinical and clinical applications", *Current Opinion in Molecular Therapeutics*, 2(4), (2000), 422-440.

Springer, C. J., "Chapter 2—Introduction to Vectors for Suicide Gene Therapy", *Methods in Molecular Medicine, vol. 90, Suicide Gene Therapy: Methods and Reviews*, (Humana Press, Inc., Totowa, NJ), (2003), 29-45.

Tachi, Y, et al., "Drug release from functionalized oligodeoxynucleotide by photo-induced electron transfer", *Nucleic Acids Symposium Series* No. 48, (2004), 79-80.

Tsourkas, A., et al., "Shedding light on health and disease using molecular beacons", *Briefings in Functional Genomics and Proteomics*, 1(4), (Jan. 2003), 372-384.

Ahmed, J., et al., "Three-dimensional analysis of pulmonary venous ostial and antral anatomy: implications for balloon catheter-based pulmonary vein isolation.", J Cardiovasc Electrophysiol., 17(3), (Mar. 2006), 251-5.

Saliba, Wilber W., et al., "Circumferential ultrasound ablation for pulmonary vein isolation: analysis of acute and chronic failures", J. Cardiovasc. Electrophysiol, (Oct. 2002), Abstract.

Terzaghi, W B., et al., "Light-Regulated Transcription", Annual Review of Plant Physiology and Plant Molecular Biology, 46, (1995), 445-474.

Williams, M. R., et al., "Alternative energy sources for surgical atrial ablation", J. Card. Surg., 19:201, (May-Jun. 2004), Abstract.

"European Application Serial No. 08795470.7, Office Action mailed Feb. 13, 2012", 6 pgs.

"Japanese Application Serial No. 2010-521875, Office Action mailed Feb. 23, 2012", 13 pgs.

"European Application Serial No. 08795470.7, Response filed Jun. 13, 2012 to Office Action mailed Feb. 13, 2012", 15 pgs.

"Japanese Application No. 2010-521875, Response filed May 18, 2012 to Non Final Office Action dated Feb. 23, 2012", English Claims with response, 15.

"Japanese Application Serial No. 2010-521875, Examiners Decision of Final Refusal mailed Jun. 28, 2012", With English Translation, 8 pgs.

* cited by examiner

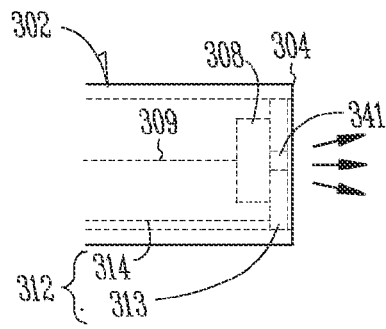
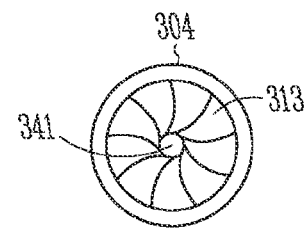
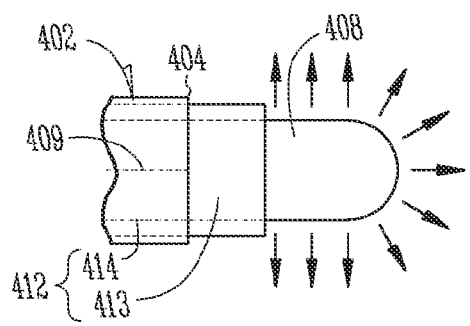
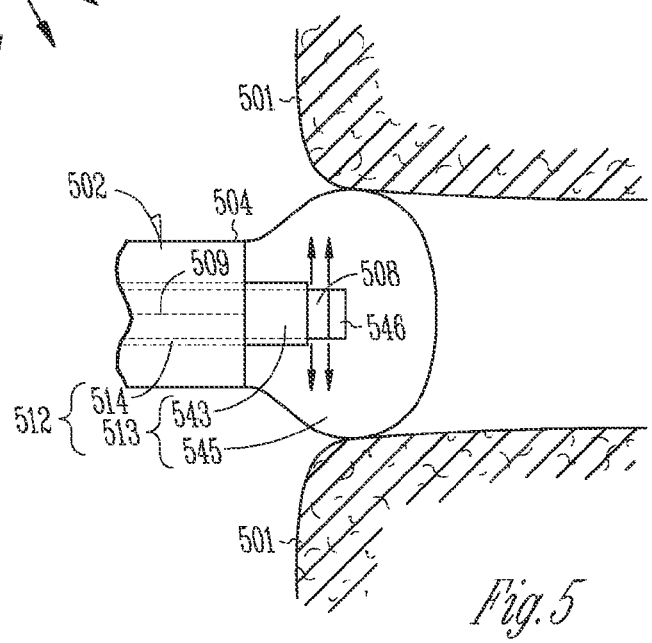
Fig. 3A
Fig. 3B
Fig. 4
Fig. 5

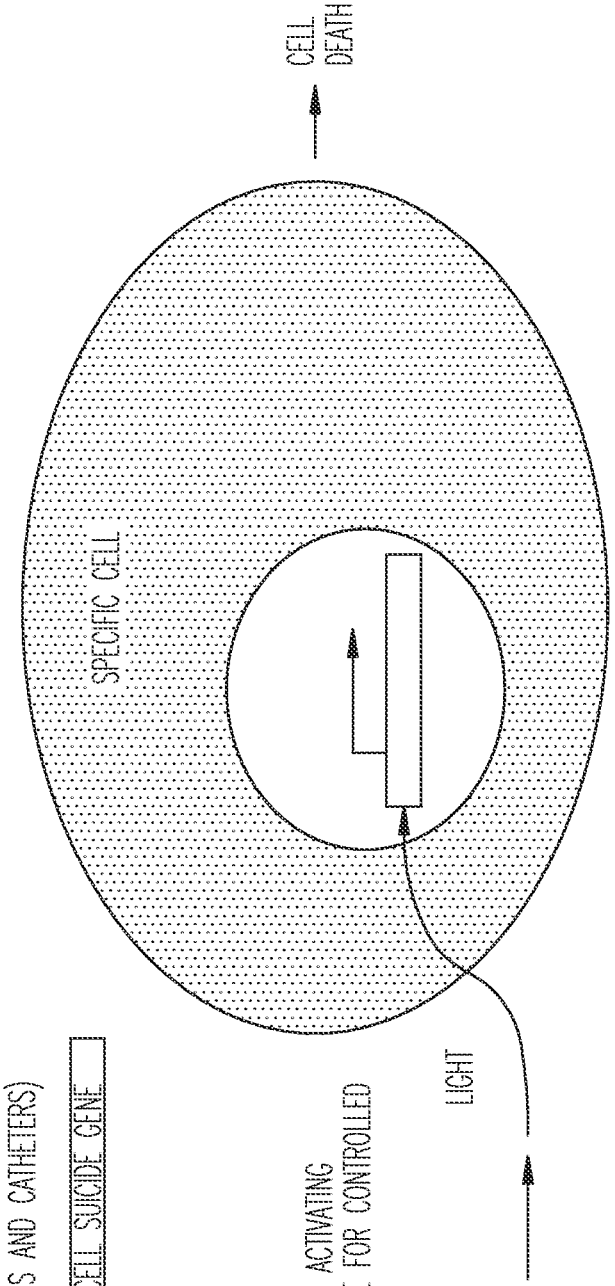

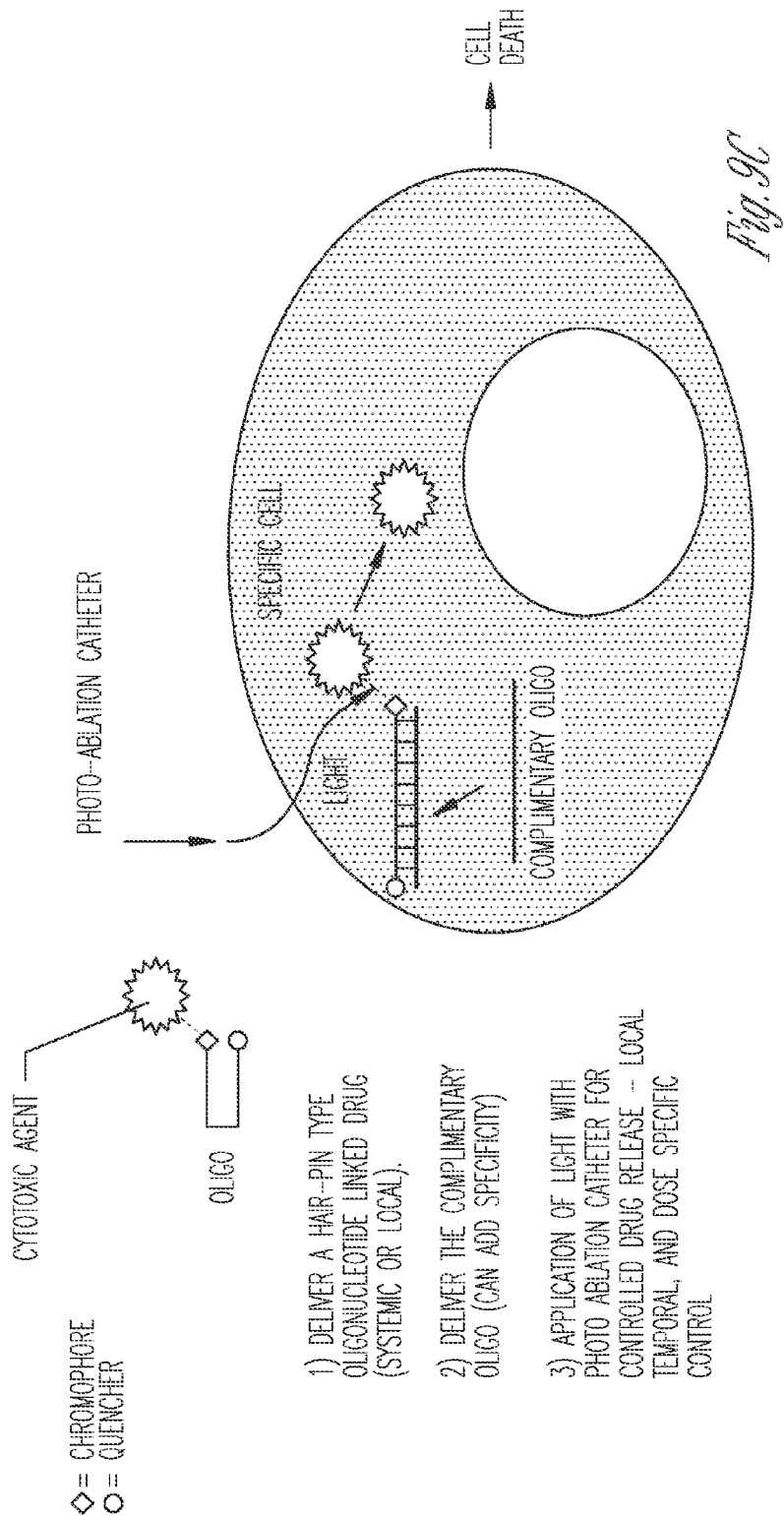

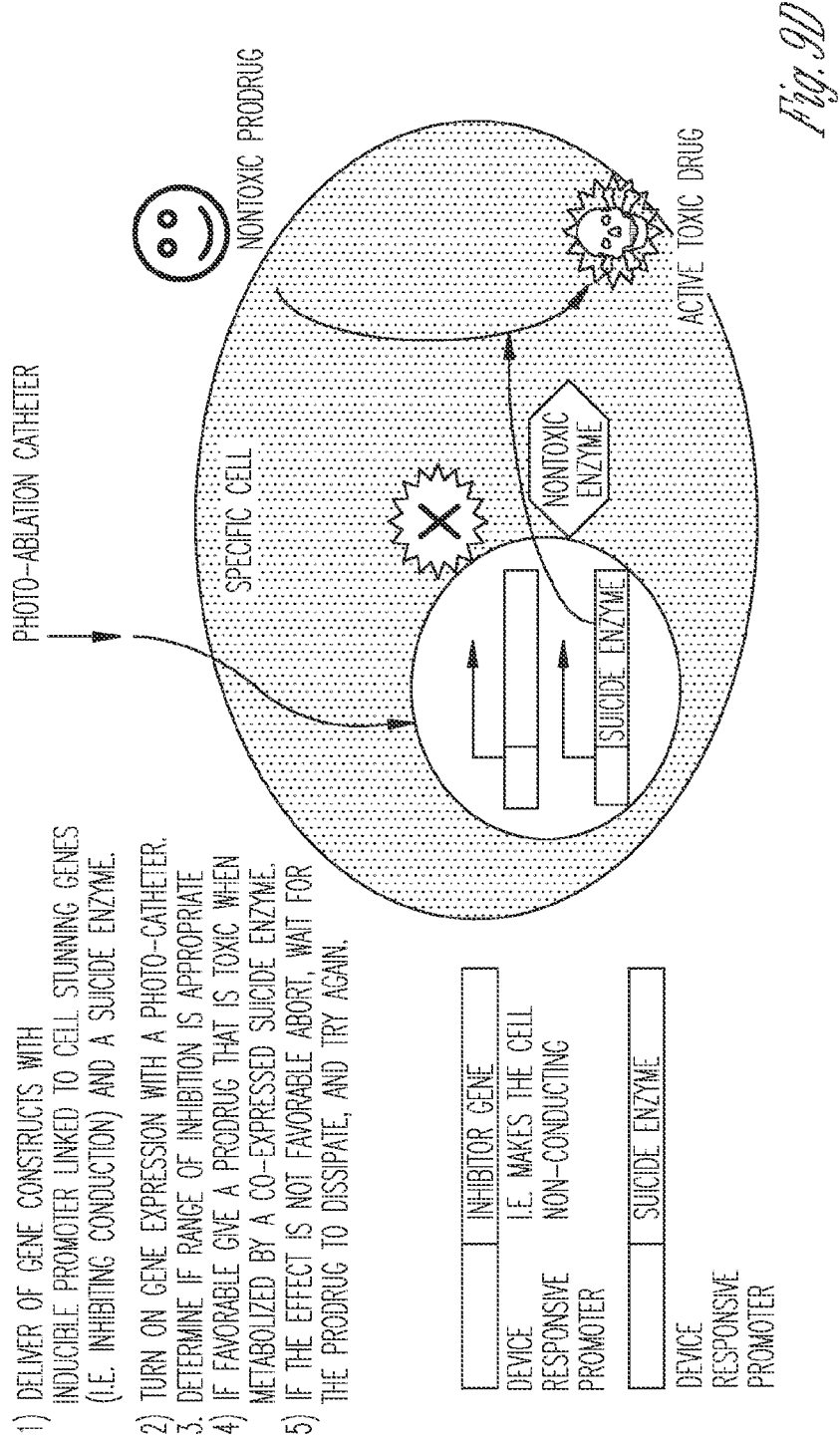

SYSTEMS AND DEVICES FOR PHOTOABLATION

FIELD OF THE INVENTION

This invention related generally to the field of ablative therapy and more specifically to ablation therapy for treating cardiac arrhythmias.

BACKGROUND

Atrial tachyarrhythmias (AT) affect many people and the quality of their lives. For instance, atrial fibrillation (AF) affects an estimated 2.3 million people in the United States. AF is a condition in which control of heart rhythm is taken away from the normal sinus node pacemaker by rapid activity (400-600 pulses per minute in humans versus about 60 beats/minute at rest or 180-200 beats/minute at peak exercise) in different areas within the upper chambers (atria) of the heart. This results in rapid and irregular atrial activity and, instead of contracting, the atria quiver. It is the most common chronic cardiac rhythm disturbance in humans and represents a major clinical problem with serious morbidity and mortality. AF requires a trigger and an atrial substrate to perpetuate AF. Eliminating the trigger or altering the substrate may reduce the incidence of AF. A substrate that perpetuates AF may involve the wavelength (conduction velocity, CV; and effective refractory period, ERP). Altering either CV or ERP may change the substrate necessary to maintain AF. Moreover, short atrial ERPs contribute to the substrate for multiple reentrant wavelets that sustain AF.

Pharmacological and device therapies have not been satisfactory to treat AF, as they have varying degrees of efficacy as well as side effects and complications. Cardiac arrhythmias have been treated traditionally with antiarrhythmic drugs that control the rhythm by altering cardiac electrical properties. However, the available drugs are not specific for atrial electrical activity and can have profound effects on ventricular electrophysiology. For example, K channel blocking drugs that are used to treat AF can mimic potentially lethal congenital disorders of the cardiac repolarization (Such as "torsade-de-pointes"). Moreover, it has become apparent over the last 20 years that the effects of antiarrhythmic drugs on the electrophysiology of the ventricles can themselves paradoxically lead to life-threatening rhythm disorders (proarrhythmia) and increase mortality. Further, drug therapy has only about 60% efficacy. There has been, therefore, a shift towards non-pharmacological therapies for cardiac arrhythmias, including controlled destruction of arrhythmia-generating tissue ("ablation therapy") and implantable devices that can sense arrhythmias and terminate them with controlled electrical discharges. However, catheter-based therapies have less than ideal efficacy and are often very time consuming due to the need to maintain adequate catheter position and contact for extended times, inconsistency in the extent of ablation with distance from the site of delivery, and multiple ablations are generally required to form the desired physical extent of ablation. In contrast to other cardiac arrhythmias, AF continues to be challenge for both pharmacological and non-pharmacological approaches to treatment.

SUMMARY OF THE INVENTION

The present invention provides compositions, devices, methods and systems useful to ablate selected tissue. In one embodiment, an ablative component in inactive form is delivered to a mammal, e.g., a photosensitive ablative component is delivered locally to a selected tissue, then a triggering component is delivered, such as light delivered by a catheter, to the tissue or cells to be ablated. The triggering component converts the ablation component to an active form, thereby resulting in ablation of cells having the ablation component. One general benefit of such a system is that delivery of the triggering component may be much faster and more accurate than current ablative therapies. Moreover, once triggered, the ablation may take place either quickly or slowly over time, depending on the nature of the ablative component and length of time and area to which the triggering component is delivered. Further, delivery of the triggering component does not require extended positioning or contact of a catheter. The ablation may be temporary so that once the arrhythmia is terminated, normal conduction may be resumed.

In one embodiment, the composition, devices, methods and systems of the invention are useful to prevent, inhibit or treat cardiac arrhythmias. In one embodiment, the composition, devices, methods and systems of the invention are useful to prevent, inhibit or treat aberrant electrically active cells or tissue, e.g., to ablate cardiac myocardium, nerves or neural tissue. In one embodiment, a catheter is employed to deliver a material to "mark" an area to be ablated, and then light is delivered to ablate only the "marked" tissue. The delivery of light produces little heat, and so reduces the clot risk in treated mammals. Moreover, treatment of more well-defined lesions may improve efficacy and may reduce procedure time. Further, depending on the wavelength of light needed for ablation, the catheter need not be in contact with tissue during ablation. In one embodiment, the invention provides a method to prevent, inhibit or treat atrial fibrillation (AF). The method includes comprising: administering to a mammal having or at risk of AF a caged photolabile toxin. An effective amount of light is delivered to a selected cardiac region of the mammal.

In one embodiment, the invention provides a method to prevent, inhibit or treat AF. The method includes administering to a mammal having or at risk of AF, an expression cassette comprising a device regulatable transcription control element operably linked to a nucleic acid sequence for a gene product. The expression of the gene product in cells directly or indirectly kills the cells. A regulatory signal from a device is capable of increasing expression from the regulatable transcription control element. A regulatory signal is delivered to a selected cardiac region of the mammal in an amount effective to prevent, inhibit or treat AF. In one embodiment, the regulatory signal is delivered by an interventional cardiac device. For example, a light signal is delivered by an interventional cardiac device. In one embodiment, the gene product is cytotoxic. In one embodiment, the expression cassette also includes a tissue-specific transcription control element, e.g., a cardiac-specific transcription control element. In one embodiment, the expression cassette is systemically delivered. In one embodiment, the selected region is a region to which the expression cassette is locally administered. In one embodiment, the expression cassette is administered to an artery. In another embodiment, the expression cassette is injected into the atria of the mammal. In one embodiment, a viral vector delivers the expression cassette to the mammal.

The invention provides a method to prevent, inhibit or treat AF. The method includes administering to a mammal having or at risk of AF a caged photolabile toxin, and delivering an effective amount of one or more selected wavelengths of light to a selected cardiac region of the mammal. In one embodiment, the caged photolabile toxin is systemically administered. In one embodiment, the caged photolabile toxin is locally administered. In one embodiment, the light signal is delivered by an interventional cardiac device.

In one embodiment, the invention provides a method to prevent, inhibit or treat AF. The method includes administering to a mammal having or at risk of AF, a first moiety comprising a quencher linked to a first oligonucleotide with a nucleotide sequence that forms a hairpin linked to a photosensitive linker linked to a cytotoxic agent, e.g., a toxin. The quencher blocks photolysis of the photosensitive linker. A second moiety is also administered. The second moiety includes a second oligonucleotide capable of forming a double stranded base paired molecule with the nucleotide sequence in the first oligonucleotide. The binding of the second moiety to the oligonucleotide displaces the quencher and exposure of the photosensitive linker to light cleaves the photosensitive linker, yielding an effective amount of the cytotoxic agent. In one embodiment, the first moiety is systemically administered. In one embodiment, the first moiety is locally administered. In one embodiment, the light is delivered by an interventional cardiac device.

In one embodiment, the invention provides a method to prevent, inhibit or treat AF. The method includes administering to a mammal having or at risk of AF, a first moiety comprising a quencher linked to a first oligonucleotide with a nucleotide sequence that forms a hairpin linked to a chromophore or fluorophore linked to a photosensitive linker linked to a cytotoxic agent. The quencher may block photolysis of the photosensitive linker or fluorescence of the fluorophore. A second moiety is also administered. The second moiety includes a second oligonucleotide capable of forming a double stranded base paired molecule with the nucleotide sequence in the first oligonucleotide. In one embodiment, the presence of the chromophore or fluorophore in the cells of the mammal is detected after administration of the second moiety. Light is delivered to cells that have the chromophore or fluorophore, so as to cleave the photosensitive linker, yielding an effective amount of the cytotoxic agent. In one embodiment, the energy emitted by the fluorophore cleaves the photosensitive linker. In one embodiment, the first moiety is systemically administered. In one embodiment, the first moiety is locally administered. In one embodiment, the light is delivered by an interventional cardiac device.

BRIEF DESCRIPTION OF THE FIGURES

FIGS. 3A-B are illustrations of an embodiment of a distal portion of the optical ablation catheter.

FIG. 4 is an illustration of another embodiment of a distal portion of the optical ablation catheter.

FIG. 5 is an illustration of another embodiment of a distal portion of the optical ablation catheter.

FIGS. 9A-D illustrate schematics of systems of the invention.

DETAILED DESCRIPTION OF THE INVENTION

Definitions

Figure 1:
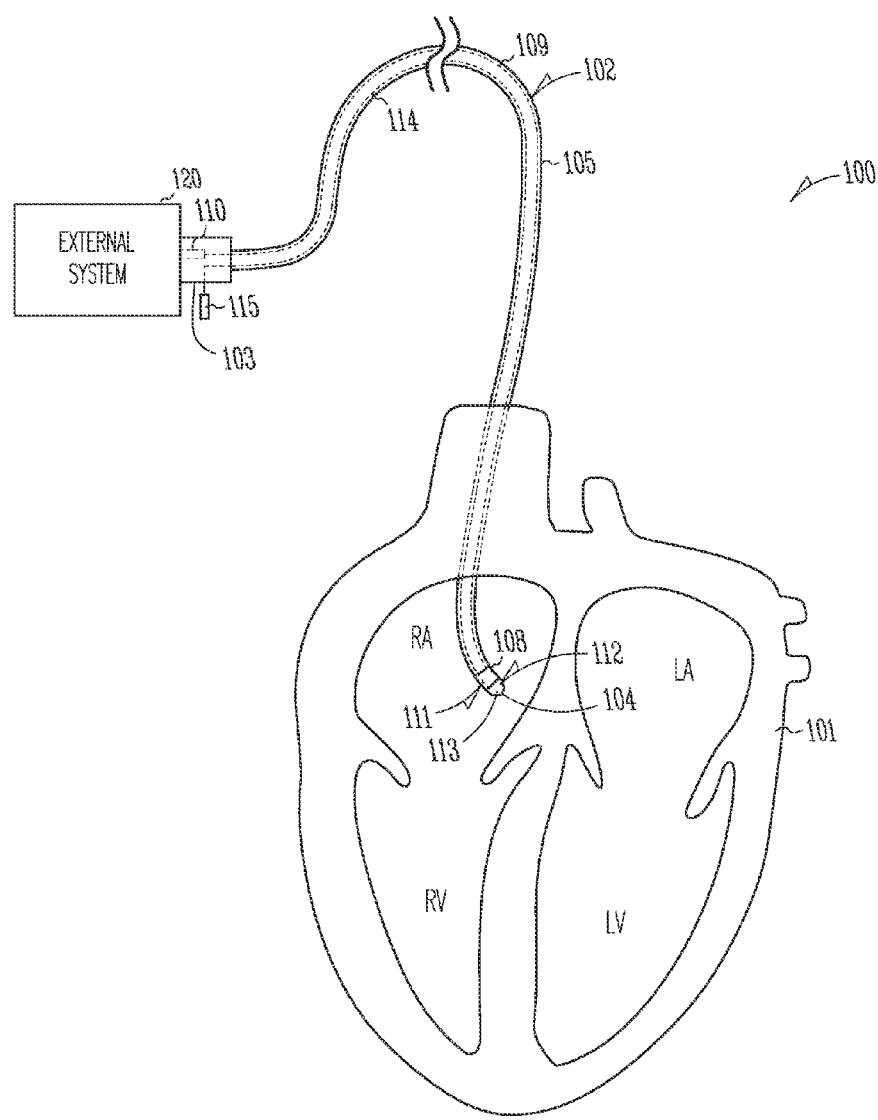
FIG. 1 is an illustration of an embodiment of an optical ablation system.

By "nucleic acid", "oligonucleotide", and "polynucleotide" or grammatical equivalents herein means at least two nucleotides covalently linked together.

"Recombinant," as applied to a polynucleotide, means that the polynucleotide is the product of various combinations of cloning, restriction and/or ligation steps, and other procedures that result in a construct that is distinct from a polynucleotide found in nature. Recombinant as applied to a protein means that the protein is the product of expression of a recombinant polynucleotide.

"In vivo" gene/protein delivery, gene/protein transfer, gene/protein therapy and the like as used herein, are terms referring to the introduction of an exogenous (isolated) polynucleotide or protein directly into the body of an organism, such as a human or non-human mammal, whereby the exogenous polynucleotide or protein is introduced to a cell of such organism in vivo.

The term "corresponds to" is used herein to mean that a polynucleotide or protein sequence is homologous (i.e., may be similar or identical, not strictly evolutionarily related) to all or a portion of a reference polynucleotide or protein sequence. In contradistinction, the term "complementary to" is used herein to mean that the complementary polynucleotide sequence is able to hybridize to the other strand. As outlined below, preferably, the homology between the two sequences is at least 70%, preferably 85%, and more preferably 95%, identical.

The terms "substantially corresponds to" or "substantial identity" or "homologous" as used herein denotes a characteristic of a nucleic acid or protein sequence, wherein a nucleic acid or protein sequence has at least about 70% sequence identity as compared to a reference sequence, typically at least about 85% sequence identity, and preferably at least about 95% sequence identity, as compared to a reference sequence. The reference sequence may be a subset of a larger sequence, such as a portion of a gene or flanking sequence, or portion of protein. However, the reference sequence is at least 20 nucleotides long, typically at least about 30 nucleotides long, and preferably at least about 50 to 100 nucleotides long, or, for peptides or polypeptides, at least 7 amino acids long, typically at least 10 amino acids long, and preferably at least 20 to 30 amino acids long. "Substantially complementary" as used herein refers to a nucleotide sequence that is complementary to a sequence that substantially corresponds to a reference sequence.

"Specific hybridization" is defined herein as the formation of hybrids between a polynucleotide which may include substitutions, deletion, and/or additions as compared to a reference sequence and a selected target nucleic acid sequence, wherein the polynucleotide preferentially hybridizes to a target nucleic acid sequence such that, for example, at least one discrete band can be identified on a Northern or Southern blot of DNA prepared from cells that contain the target nucleic acid sequence. It is evident that optimal hybridization conditions will vary depending upon the sequence composition and length(s) of the polynucleotide(s) and target(s), and the experimental method selected by the practitioner. Various guidelines may be used to select appropriate hybridization conditions.

"Treatment" or "therapy" as used herein refers to administering, to an individual patient, agents that are capable of eliciting a prophylactic, curative or other beneficial effect in the individual.

"Gene therapy" as used herein refers to administering, to an individual patient, vectors comprising a gene encoding a beneficial gene product.

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a sequence of interest for gene therapy. Vectors include, for example, transposons and other site-specific mobile elements, viral vectors, e.g., adenovirus, adeno-associated virus (AAV), poxvirus, papillomavirus, lentivirus, herpesvirus, foamivirus and retrovirus vectors, and including pseudotyped viruses, liposomes and other lipid-containing complexes, and other macromolecular complexes capable of mediating delivery of a polynucleotide to a host cell, e.g., DNA coated gold particles, polymer-DNA complexes, liposome-DNA complexes, liposome-polymer-DNA complexes, virus-polymer-DNA complexes, e.g., adenovirus-polylysine-DNA complexes, and antibody-DNA complexes. Vectors can also comprise other components or functionalities that further modulate gene delivery and/or gene expression, or that otherwise provide beneficial properties to the cells to which the vectors will be introduced. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described (see, e.g., Curiel et al., *Proc. Natl. Acad. Sci. USA*, 88:8850 (1991)).

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, iontophoresis, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the organism if integrated into the genome or maintained extrachromosomally. Such a transgene may include a gene which is partly or entirely heterologous (i.e., foreign) to the transgenic organism, or may represent a gene homologous to an endogenous gene of the organism.

By "transgenic cell" is meant a cell containing a transgene. For example, a stem cell transformed with a vector containing an expression cassette can be used to produce a population of cells having altered phenotypic characteristics.

The term "wild-type" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

"Vasculature" or "vascular" are terms referring to the system of vessels carrying blood (as well as lymph fluids) throughout the mammalian body.

"Blood vessel" refers to any of the vessels of the mammalian vascular system, including arteries, arterioles, capillaries, venules, veins, sinuses, and vasa vasorum.

"Artery" refers to a blood vessel through which blood passes away from the heart. Coronary arteries supply the tissues of the heart itself, while other arteries supply the remaining organs of the body. The general structure of an artery consists of a lumen surrounded by a multi-layered arterial wall.

The term "transduction" denotes the delivery of a polynucleotide to a recipient cell either in vivo or in vitro, via a viral vector, e.g., via a replication-defective viral vector, such as via a recombinant adenovirus or AAV.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

By "DNA" is meant a polymeric form of deoxyribonucleotides (adenine, guanine, thymine, or cytosine) in double-stranded or single-stranded form found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence complementary to the mRNA). The term captures molecules that include the four bases adenine, guanine, thymine, or cytosine, as well as molecules that include base analogues which are known in the art.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

A "polynucleotide" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA, and portions of both double stranded or single stranded sequence. The polynucleotide may be DNA, both genomic and cDNA, RNA or a hybrid, where the polynucleotide contains any combination of deoxyribo- and ribo-nucleotides, and any combination of bases, including uracil, adenine, thymine, cytosine, guanine, inosine, xathanine and hypoxathanine, etc. Thus, for example, chimeric DNA-RNA molecules may be used such as described in Cole-Strauss et al., *Science,* 273:1386 (1996) and Yoon et al., *Proc. Natl. Acad. Sci. USA,* 93:2071 (1996). It also includes modified polynucleotides such as methylated and/or capped polynucleotides.

A "gene," "polynucleotide," "coding region," or "sequence" which "encodes" a particular gene product, is a nucleic acid molecule which is transcribed and optionally also translated into a gene product, e.g., an antisense sequence or a polypeptide, in vitro or in vivo when placed under the control of appropriate regulatory sequences. The "coding" region may be present in either a cDNA, genomic DNA, RNA form, or a hybrid. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. Thus, a gene includes a polynucleotide which may include a full-length open reading frame which encodes a gene product (sense orientation) or a portion thereof (sense orientation) which encodes a gene product with substantially the same activity as the gene product encoded by the full-length open reading frame, the complement of the polynucleotide, e.g., the complement of the full-length open reading frame (antisense orientation) and optionally linked 5' and/or 3' noncoding sequence(s) or a portion thereof, e.g., an oligonucleotide, which is useful to inhibit transcription, stability or translation of a corresponding mRNA. A transcription termination sequence will usually be located 3' to the gene sequence.

An "oligonucleotide" includes at least 7 nucleotides, preferably 15, and more preferably 20 or more sequential nucleotides, up to 100 nucleotides, either RNA or DNA, which correspond to the complement of the non-coding strand, or of the coding strand, of a selected mRNA, or which hybridize to the mRNA or DNA encoding the mRNA and remain stably bound under moderately stringent or highly stringent conditions, as defined by methods well known to the art, e.g., in Sambrook et al., A Laboratory Manual, Cold Spring Harbor Press (1989).

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence. Thus, a "promoter," refers to a polynucleotide sequence that controls transcription of a gene or coding sequence to which it is operably linked. A large number of promoters, including constitutive, inducible and repressible promoters, from a variety of different sources, are well known in the art.

By "enhancer element" is meant a nucleic acid sequence that, when positioned proximate to a promoter, confers increased transcription activity relative to the transcription activity resulting from the promoter in the absence of the enhancer domain. Hence, an "enhancer" includes a polynucleotide sequence that enhances transcription of a gene or coding sequence to which it is operably linked. A large number of enhancers, from a variety of different sources are well known in the art. A number of polynucleotides which have promoter sequences (such as the commonly-used CMV promoter) also have enhancer sequences.

By "cardiac-specific enhancer or promoter" is meant an element, which, when operably linked to a promoter or alone, respectively, directs gene expression in a cardiac cell and does not direct gene expression in all tissues or all cell types. Cardiac-specific enhancers or promoters may be naturally occurring or non-naturally occurring. One skilled in the art will recognize that the synthesis of non-naturally occurring enhancers or promoters can be performed using standard oligonucleotide synthesis techniques.

"Operably linked" refers to a juxtaposition, wherein the components so described are in a relationship permitting them to function in their intended manner. By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. Thus, a signal or targeting peptide sequence is operably linked to another protein if the resulting fusion is secreted from a cell as a result of the presence of a secretory signal peptide or into an organelle as a result of the presence of an organelle targeting peptide.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

By "expression construct" or "expression cassette" is meant a nucleic acid molecule that is capable of directing transcription. An expression construct includes, at the least, a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial or natural means, or in relation a cell refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide, polypeptide or virus refers to a nucleic acid sequence, peptide, polypeptide or virus that is identified and separated from at least one contaminant nucleic acid, polypeptide, virus or other biological component with which it is ordinarily associated in its natural source. Isolated nucleic acid, peptide, polypeptide or virus is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

The term "peptide", "polypeptide" and protein" are used interchangeably herein unless otherwise distinguished to refer to polymers of amino acids of any length. These terms also include proteins that are post-translationally modified through reactions that include glycosylation, acetylation and phosphorylation.

"Gene regulation" or "Gene regulatory therapy" as used herein includes delivery of one or more gene regulatory signals to regulate gene expression in a gene therapy vector. The gene regulatory signals include signals that trigger a transcriptional control element, e.g., a promoter.

General Overview

Figure 9A:
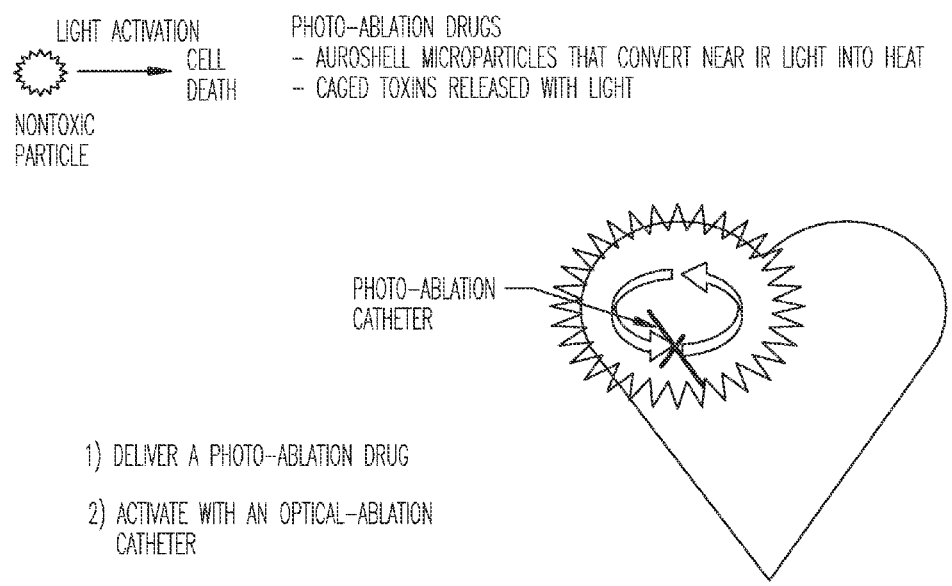

The invention provides therapeutic compositions, devices, systems and methods useful to ablate cells or tissue. In one embodiment, an ablative component is administered to the tissue in an inactive form, which inactive form is activated by a triggering component. For instance, the ablative component may be a moiety that generates heat upon exposure to a triggering component, e.g., infrared light (FIG. 9A). In one embodiment, the composition for use with a device or in the methods of invention, includes AuroShell™ microparticles. AuroShell™ microparticles when illuminated with near-infrared light, such as that emitted from a laser, absorb the light and convert it into heat.

In one embodiment, the composition for use with a device or in the methods of the invention, includes an ablative component that is a toxic molecule that is inactive due to being bound to a molecular cage (FIG. 9A). The cage is released upon exposure to a triggering component, such as exposure to certain molecules or conditions, e.g., light of a particular wavelength or band of wavelengths. Once the triggering component is delivered to the tissue to be ablated, the inactive toxic molecule is converted to an active form, and cells with the toxin are ablated.

In one embodiment, the composition for use with a device or in the methods of the invention, includes an ablative component that is an expression cassette having a regulatable transcription control element, e.g., one regulated by light of a particular wavelength or band of wavelengths, linked to a nucleic acid encoding cytotoxic gene product, e.g., a cell suicide gene, that is expressed upon exposure to a triggering component, e.g., exposure to light (FIG. 9B).

In one embodiment, the invention provides a method to prevent, inhibit or treat AF. The method includes administering to a mammal having or at risk of AF, a first moiety comprising a quencher linked to a first oligonucleotide with a nucleotide sequence that forms a hairpin linked to a photosensitive linker linked to a cytotoxic agent. The quencher blocks photolysis of the photosensitive linker. Quenchers and photosensitive linkers are known to the art, e.g., see U.S. Pat. Nos. 4,650,770, and 5,470,307, U.S. published application Nos. 20060142853 and 20060034943, Akerbloom et al. (*Mol. Div.*, 3:137 (1997)), Gryczynski et al. (*J. Biomed. Optics*, 2:80 (1997)), McGlennen et al. (*Clin. Chem.*, 47:3393 (2001)), Kochetor et al. (*Rus. Chem. Rev.*, 69:795 (2000)) and Kusba et al. (*Biophys. J.*, 67:2024 (1994)). A second moiety is also administered. The second moiety includes a second oligonucleotide capable of forming a double stranded base paired molecule with the nucleotide sequence in the first oligonucleotide. The binding of the second moiety to the oligonucleotide displaces the quencher and exposure of the resulting complex to light cleaves the photosensitive linker yielding an effective amount of the cytotoxic agent.

In another embodiment, the composition for use with a device or in the methods of the invention, includes an ablative component that is an oligonucleotide having a nucleotide sequence capable of forming a hairpin structure, a quencher attached to one end of the oligonucleotide, and a complex attached to the other end of the oligonucleotide. The complex may include a chromophore or fluorophore, the detection of which may be quenched by the quencher when a hairpin is formed, a photocleavable linker, and a toxic agent. A second agent with a nucleic acid sequence having the complement of the hairpin sequence is administered. In one embodiment, after administration of the second agent, the presence of the chromophore or fluorophore in the cells of the mammal is detected. Light is delivered to cells that have the chromophore or fluorophore, so as to cleave the photosensitive linker, releasing the cytotoxic agent. In one embodiment, the energy emitted by the fluorophore cleaves the photosensitive linker (FIG. 9C).

In another embodiment, the composition for use with a device or in the methods of the invention, includes an ablative component that is a vector system having two expression cassettes (FIG. 9D). In one embodiment, the expression cassettes are in tandem on the same vector, e.g., plasmid or viral vector. In another embodiment, the expression cassettes are on different vectors. In one embodiment, both expression cassettes have the same regulatable transcription control element, one operably linked to a nucleic acid encoding a gene product that inhibits conduction, and the other operably linked to a nucleic acid encoding a suicide enzyme which interacts with a prodrug, yielding a cytotoxic agent In another embodiment, one expression cassette has a first regulatable transcription control element linked to a nucleic acid encoding gene product that is an inhibitor of conduction, and the other has a second regulatable transcription control element which is different than the first regulatable transcription control element, linked to a nucleic acid encoding the suicide enzyme. Nucleic acid encoding inhibitors of conduction include, but are not limited to, those disclosed in U.S. application entitled "SYSTEMS FOR TRANSIENT CONDUCTION CONTROL", filed on evendate herewith, and commonly assigned. Expression of the inhibitor inhibits conduction in cells, and if it is determined that the inhibition is sufficient, e.g., using an active test such as electrophysiology testing (by stimulating the heart to trigger an irregular heart beat or halting an irregular heart beat) and mapping the EP test (with electrodes that map the spread of electrical impulses in the heart), or a stress test, or passive tests, such as an ECG, Holter monitor, or an echocardiogram, a prodrug for the suicide enzyme is administered and expression from the second cassette in the same cell as the first cassette results in a suicide enzyme which metabolizes the prodrug.

Exemplary Ablative Components

In one embodiment, the ablative component is a toxic agent, e.g., diphtheria toxin, ricin, *Pseudomonas* exotoxin, pertussis toxin, pokeweed antiviral protein, abrin, RNase, DNase, botulin, saponin and the like that is bound in or to a photosensitive molecular cage, thereby rendering the toxin inert. Caged compounds are synthetic molecules whose biological activity is controlled by light, usually by photolytic conversion from an inactive to an active form. Generally, simple covalent bond formation masks some feature important for activity. Photochemical cleavage of that single bond releases the active species.

Caged compounds are most commonly designed by modifying the desired biomolecule with a suitable photoremovable protecting group or caging group. To be useful in biological experiments this group must satisfy (at least partially) several criteria: (a) it should render the biomolecule inert to the biological system used, (b) it should release the biomolecule in high yield at sufficient speed by photolysis at wavelengths of light that are non-detrimental to the biological preparation, (c) any photoproducts other than the desired biomolecule should not interact or interfere with the biological system. Several different caging groups have been described, including 2-nitrobenzyl groups. Caging groups based on the photoisomerization of 2-nitrobenzyl substituents are by far the most prevalent in present caged compounds. Their advantages including compatibility with a wide variety of functional groups (e.g., phosphates, carboxylates, hydroxyl groups, amines and amides), ease of synthesis, and reasonable light sensitivity and kinetics. The 4,-5-dimethoxy-2-nitrobenzyl (DMNB) cage has higher absorbance in 350 to 400 nm.

Exemplary photolabile cage groups include 2-nitrobenzyl (NB), 2-(2-nitrophenyl)ethyl) (NPE), α-carboxy-2-nitrobenzyl (CNB), 2,2'-dinitrobenzhydryl (DNB), 4,5-dimethoxy-2-nitrobenzyl (DMNB), 2-(4,5-dimethoxynitrohpenyl)ethyl (DMNPE), bis(2-nitro-4,5-dimethoxyphenyl)methyl, α-benzoyl-3,5-dimethoxybenzyl, 3,5-dinitrophenyl, (4-methoxy-8-azido-1-naphthyl)methyl, 5,7-dinitroindolinyl, and 4-methoxyphenacyl. α-carboxy-2-nitrobenzyl or a CNB protecting group is useful to cage glycines, and DNB is useful as a caging group for phosphates, carboxylates, and hydroxyls. Bis(2-nitro-4,5-dimethoxyphenyl)methyl group is a more photosensitive group.

Many of these groups require photolysis with short wavelength ultraviolet light (<300 nm). However, some have been designed to work at longer wavelengths to prevent photodestruction of amino acids such as tryptophan and tyrosine. Substituted benzoin esters (for example, containing the α-benzoyl-3,5-dimethoxybenzyl group), are potential photosensitive protecting groups for carboxylates and also for protecting phosphate groups. α-Benzoyl-3,5-dimethoxybenzyl phosphate absorbs between 340 to 360 nm. 3-nitrophenyl ester and its derivatives such as 3,5-dinitrophenyl are phosphate cages. 3,5-Dinitrophenyl (DNP) is converted by irradiation at 300-360 nm. Other protecting groups for photogeneration of carboxylates include (azidonaphthyl)methyl esters. Another group that utilizes photosolvolysis for the release of carboxylates is 5,7-dinitroindolinylamide. This can be irradiated at wavelengths beyond 400 nm. Methoxyphenacyl groups may be carboxyl-photosensitive protecting groups that can be photolyzed by irradiation of greater than 330 nm.

For instance, photolabile protecting groups have been used to cage the biological activity of a wide variety of molecules. These caged species can be loaded into cells in an inactive form. Subsequently, the intracellularly loaded compounds can be photolyzed (when desired and in a spatially localized fashion). Some caged compounds have been prepared with alkylating agents derived from various incarnations of the ortho-nibrobenzyl functionality 1. Light-induced transformation of α-heteroatom (X=O, S, N) substituted ortho-nitrobenzyl derivatives (1) to ortho-nitroso derivatives (3). R can be a variety of moieties (e.g., CH$_3$, CO$_2^-$, etc.) and R' represents the compound/protein that has been caged.

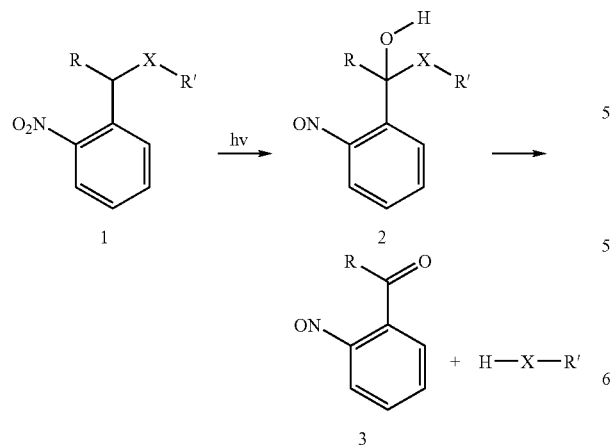

High intensity UV-visible radiation promotes an oxygen transfer from the nitro moiety to the benzylic position. The benzylic position is substituted with a heteroatom (X=N, S or O), and therefore oxygen transfer generates an unstable hemiacetal that decomposes to furnish the uncaged (and biologically active) species shown as H—X—R. Other caging molecules include:

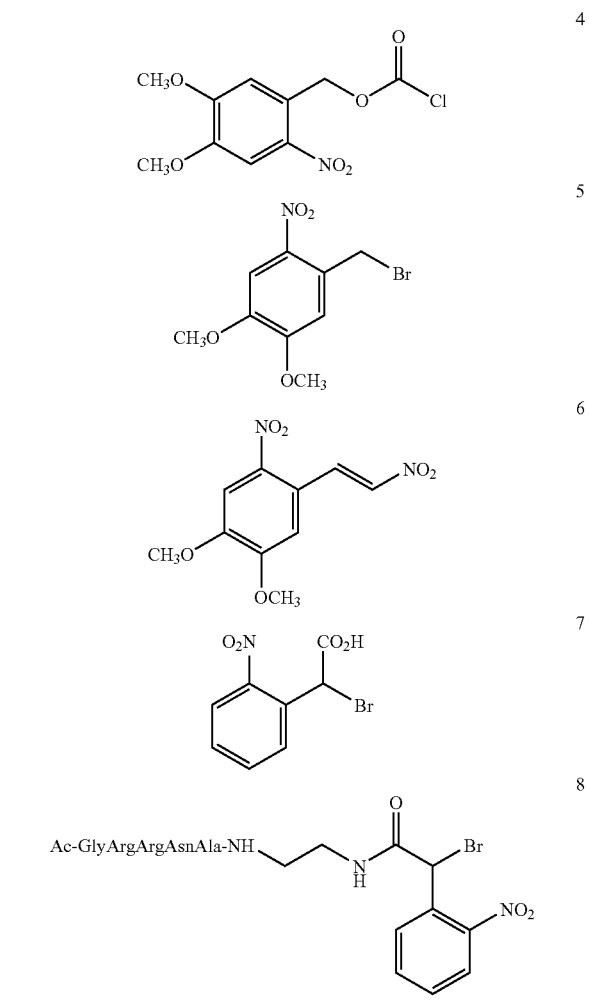

The majority of caged proteins and enzymes to date are activated via the general mechanism outlined above, which is dependent upon the presence of ortho-nitrobenzyl functionality. One of the earliest different light-initiated processes are inactivated with para-amidinophenyl-ortho-hydroxymethyl-cinnimate (9), which forms a stable acyl enzyme intermediate (10) upon release of the para-amidinophenol leaving group. Photoisomerization to the cis derivative (11), however, positions the aromatic hydroxyl group adjacent to the ester of the acyl enzyme, which in turn promotes the intramolecular regeneration of the free cerine hydroxyl group.

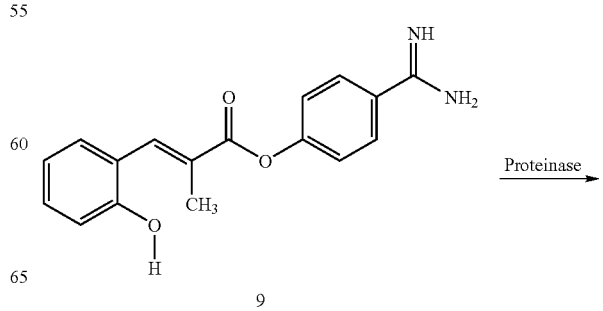

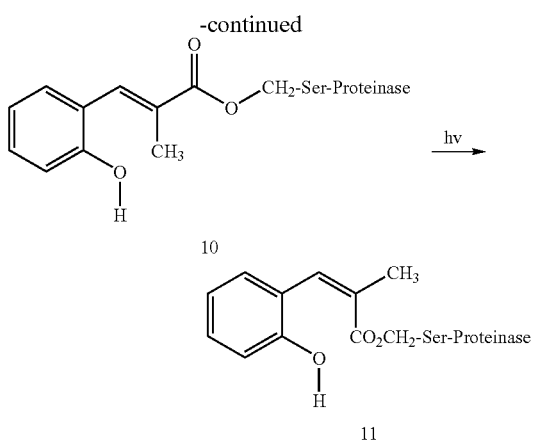

Selective or reversible permeabilization with staphylococcal α-toxin permits entry of compounds with molecular weights less than 1000, β-escin, a saponin ester, allows introduction of compounds with molecular weights up to 17,000, and the use of acetoxymethyl ester derivatives of the caged compound to permit passive diffusion across the cell membrane.

In one embodiment, the ablative component is a nanoparticle or microparticle, such as AuroShell™ microparticles, which converts certain wavelengths of light to heat. These particles may be delivered by one or more of the methods described herein and then activated for ablation with, for instance, a near infrared laser or shorter wave lengths for more precise ablation. In one embodiment, particles, e.g., AuroShell™ microparticles (see http://www.nanospectra.com/Aurolase.htm) are injected intravenously. After the particles accumulate in the tissue, they are illuminated with a near-infrared laser at wavelengths chosen to allow the maximum penetration of light through tissue.

In one embodiment, the photoinduced drug release system is a photoreactive hairpin-type oligodeoxynucleotide (P-ODN) possessing a chromophore linked to a drug via a photocleavable linker, and a quencher. In one embodiment, the chromophore is o-nitrobenzyl. In one embodiment, the quencher is 1-aminophthalene. In one embodiment, the drug is released after binding of P-ODN to its complementary DNA and photoirradiation (see, e.g., Tachi et al., *Nucleic Acids Symposium Series* 2004, 48:79 (2004) http://nass.oxfordjournals.org/cgi/content/abstract/48/1/79).

In one embodiment, the ablative component is linked to a photoinduced drug releasing system. In one embodiment, the system includes a quencher, an oligonucleotide capable of forming a stem-loop structure (hairpin), a photosensitive linker, and a cytotoxic agent. In another embodiment, the system also includes a fluorescent probe known as a "molecular beacon" which elicits a fluorogenic response only after the stem-loop structure is disrupted due to increased distance from the quencher. In one embodiment, an oligonucleotide probe with an antisense target-binding domain flanked by two complementary short arm sequences is labeled at one end with a quencher of the photosensitive linker. In the absence of a target, the short arms anneal to form a hairpin structure, forcing the quencher into close proximity with the linker. Upon hybridization with a complementary target, the hairpin structure opens, separating the quencher and linker, the latter of which is cleaved upon exposure to light. In another embodiment, an oligonucleotide probe with an antisense target-binding domain flanked by two complementary short arm sequences is labeled at one end with a reporter dye and at the opposite end with a quencher. In the absence of a target, the short arms anneal to form a hairpin structure, forcing the dye, e.g., fluorophore, into close proximity with the quencher. In this conformation, the photoinduced drug releasing system is dark. Upon hybridization with a complementary target, the hairpin structure opens, separating the dye and quencher, resulting in the restoration of the optical signal generated by the dye.

The loop usually consists of 15 to 25 nucleotides and is selected based on a target sequence, and melting temperature. The stem, formed by two complementary short arm sequences, is typically four to six bases long and is usually chosen to be independent of the target sequence. In one embodiment, one arm of the stem participates in stem formation and target hybridization. The probe and stem length and sequence are important since, at any given temperature, they largely control the fraction of the molecule that is in each of three different conformational states: bound-to-target, stem-loop and random-coil. The probe and stem lengths, and stem sequence, can be adjusted to optimize the performance (i.e., specificity, hybridization rate). Longer stem lengths are accompanied by a lower target affinity and thus a decreased photoinduced drug releasing molecule-target hybridization rate. photoinduced drug releasing molecules with short stems have faster hybridization kinetics and improved target affinities. Increasing the probe length of the molecules results in improved target affinity and increased kinetic rates, but leads to a reduced specificity. The effect of probe length on the behavior of the molecules is typically less dramatic compared with that of stem length. Organic quencher molecules such as dabcyl, BHQ, and Iowa Black all effectively quench a wide range of fluorophores. This is because quenching is based on both the formation of an exiton heterodimer (contact quenching) and fluorescence resonance energy transfer (FRET) between the fluorophore and the quencher. In addition to organic quenchers, gold nanoparticles can also be used as a quencher.

Oligonucleotide probes with phosphodiester backbones only possess a half-life of 15-20 minutes and therefore only provide limited use for in vivo detection. photoinduced drug releasing molecules possessing 2'-O-methyl-oligoribonucleotides, phosphorothioate oligonucleotides or peptide nucleic acids (PNAs) may have an improved resistance to nucleases. 2'-O-methyl molecules exhibit an improved affinity for RNA and faster hybridization kinetics compared with 2'-deoxy (unmodified) molecules. They are also known to be capable of avoiding degradation of target RNA by RNase H upon hybridization, however, 2'-O-methyl oligoribonucleotides tend to localize in the nucleus and are thus less likely to hybridize to cytoplasmic RNAs. Phosphorothioate oligonucleotides (PS-ODNs) are less likely to induce RNase H cleavage than unmodified oligonucleotides. PNAs bind complementary targets without the electrostatic repulsion that is present in unmodified nucleic acids duplexes. As a result, PNAs form more stable duplexes with DNA and RNA targets.

Gene-Directed Enzyme Prodrug Therapy

GDEPT or "suicide gene therapy," the gene encoding an enzyme is delivered to cells, followed by the systemic administration of a prodrug, which is converted locally to a cytotoxin by the enzyme. Enzyme expression can be genetically controlled or its delivery targeted to ensure selectivity. A further advantage of the GDEPT system is the ability to image the correct location and expression of the (harmless) enzyme prior to prodrug administration. The following provide exemplary GDEPT.

Gancyclovir (GCV) is a derivative of acyclovir with the addition of a methoxy group at the 3' carbon acyclic sidechain which gives increased activity. After phosphorylation by a thymine lurase such as HSV-tk, GCV undergoes a series of intracellular reactions resulting in the formation of a triphosphate. This competes with deoxyguanosine triphosphate in DNA elongation during cell division, resulting in inhibition of DNA polymerase and single-strand breaks.

Cytosine deaminase of some bacterial and fungal cells is capable of converting the less toxic 5-Fluorocytosine (5-FC) to 5-FU. 5-FU undergoes further enzymatic conversion to 5-FUTP, which is incorporated into DNA and prevents nuclear processing of ribosomal and mRNA, and to 5-fluorouridine-5'-monophosphate, which irreversibly inhibits thymidylate synthase. The toxicity of 5-FU is not cell cycle specific. The bystander effect of CD/5-FC is not dependent on gap junctions, as 5-FU is capable of non-facilitated diffusion into, and out of, cells.

Bacterial nitroreductase (NTR) can convert the relatively non-toxic monofunctional alkylating agent, CB1954 (5-aziridin-1-yl-2,4-dinitrobenzamide Glaxo Wellcome), to a bifunctional alkylating agent capable of killing non-cycling cells. CB1954 was shown to be a potent DNA cross-linking agent, causing cell death. The NTR/CB1954 combination is effective under hypoxia and anoxia and not dependent on cell proliferation.

Cyclophosphamide (CPA) and iphosphamide (IPA) are cancer chemotherapeutic prodrugs, which need to be activated by liver cytochrome (CYP) P450 enzymes. In human liver the CYP2B6 and CYP3A4 forms are catalytically active for both CPA and IPA. Metabolism of oxazophorines gives rise to a 4-hydroxy compound which is in equilibrium with its open-ring aldo-tautomer. This breaks down to a phosphoramide mustard and acrolein in equimolar amounts. The mustard is an alkylating agent able to form DNA cross-links in a cell cycle-independent manner.

Hypoxic cytotoxins, or bioreductives, are prodrugs activated within the reducing environment of the oxygen-deprived cells. The redox-sensitive flavoprotein NADPH P450R is an important activator of many bioreductives. It was shown that the toxicity of tirapazamine (TPZ), a benzotriazene-di-N-oxide, under hypoxia, was strongly correlated with P450R activity. Other bioreductives, including E09 (Saunders et al., *Biochem. Pharma.*, 59:993 (2000)) and RSU1069 (Patterson et al., *Br. J. Cancer*, 76:1338 (1967)), show increase activity. Placement of the P450R enzyme under the control of hypoxia response elements resulted in hypoxia-dependent expression.

Carboxypeptidase G2 (CPG2) is a bacterial enzyme with no human analog, able to catalyze the conversion of 4-[(2-chloroethyl)(2-mesyloxy-ethyl)amino]benzoyl-L-glutamic acid (CMDA) to the DNA cross-linking mustard, 4-[(2-chloroethyl)(2-mesyl-oxyethyl)amino]benzoic acid (Springer et al., *J. Med. Chem.*, 33:677 (1990)).

Horseradish peroxidase is a heme enzyme isolated from the roots of the horseradish plant. Indole-3-acetic Acid (IAA) is a plant auxin involved in the regulation of plant cellular growth, division and differentiation. It is also a natural metabolite in mammals of the amino acid tryptophan by monoamine oxidase. The reaction of HRP with IAA is characterized by the formation of a radical cation, which undergoes scission of the carbon-carbon bond to give a carbon-centered skatolyl radical and after subsequent toxic steps forms the toxin 3-methylene-2-oxindole (MOI).

The *E. coli* purine nucleoside phosphorylase-encoding gene has been mutated to increase substrate specificity and cleaves 9-(6-deoxy-α-L-talofuranosyl)-6-methylpurine, to a toxic agent. *E. coli* xanthine-guanine phosphoribosyltransferase (XGPRT, gpt) can convert 6-thioxanthine into its membrane-impermeable toxic monophosphorylated form. Another potent suicide gene is the product of the *E. coli* DeoD gene (purine nucleoside phosphorylase (PNP)) that is capable of converting weakly toxic deoxyadenosine analogs, such as 6-methylpurine-2'-deoxyriboside (6-MP-dR), to highly toxic adenine analogs, such as 6-methylpurine. The methionine-αγ-lyase gene from *Pseudomonas putida* may be used to convert the physiologic compound selenomethionine into the highly toxic methylselenol and, in combination. CYP4B1 may be utilized to convert the inert prodrug 4-ipomeanol into a toxic alkylating agent.

Table 1 provides an exemplary list of suicide genes for GDEPT. Suicide genes encompass any expressed protein that can make a cell specifically sensitive to a drug.

TABLE 1

| Name Abbreviation | Prodrug |
| --- | --- |
| HSV-thymidine kinase (tk) | ganciclovir (GCV) or acyclovir |
| Cytosine deaminase (CDA) + uracil phosphoribosyltransferase | 5-fluorocytosine (5-FC) |
| Xanthine-guanine phosphoribosyl-transferase (GPT) | 6-thioxantine (6-TX) |
| Nitroreductase (NTR) | CB1954 |
| Purine nucleoside phosphorylase (PNO; DeoD) | 6-MP-dR, Fludarabine |
| Cytochrome P450 (CYP4B1) | 2-aminoanthracene (2-AA) |
| Carboxypeptidase G2 (CPG2) | CMDA |
| D-amino acid oxidase (DAAO) | D-alanine |
| Carboxypeptidase A1 (CPA) | Methotrexate-α-Phe (MTX-F) |
| Deoxycytidine kinase (dCK) | Fludarabine, Ara-C |
| Cytochrome P450 (CYP2B1, 6) | Cyclophosphamide (CPA) |
| LNGFR/FKBP/Fas | CIDs |
| FKBP/Caspases | CIDs |
| ER/p53 | Tamoxifen |

For extended expression of suicide genes and for repeated administration, suicide genes based on human proteins may be superior.

In one embodiment, each gene may be linked to a regulatable transcription control element, for example, regulatable by a device controlled responsive promoter. In one embodiment, each gene may be linked to an inducible promoter (such as tetracycline responsive promoter). In one embodiment, the device controlled regulatable transcription control element is activated with light. In one embodiment, the device controlled regulatable transcription control element is activated with a chemical. In one embodiment, the device controlled regulatable transcription control element is activated with thermal energy. In one embodiment, the device controlled regulatable transcription control element is activated with electrical energy. In one embodiment, the device controlled regulatable transcription control element is activated with acoustic energy. In one embodiment, the device controlled regulatable transcription control element is activated with ultrasound or RF.

In one embodiment, a regulatable transcription central element includes a transcription control element activated by light. In one embodiment, a regulatable transcription control element is linked to a suicide gene, e.g., one encoding a cytotoxic gene product. In one embodiment, the regulatable transcription control element includes a transcription control element from human, plants, mold, an invertebrate, or is synthetic.

In one embodiment, a light activated transcription control element is derived from *Neurospora*, e.g., white collar complex. In one embodiment, the suicide enzyme is herpes simplex thymidine kinase (HSV-TK) and the prodrug is ganciclovir (GCV). In one embodiment, the suicide enzyme is *E. coli* cytosine deaminase (CD) and the prodrug is 5-fluorocytosine (5-FC). In one embodiment, the suicide enzyme is varicella zoster thymidine kinase. In one embodiment, the suicide enzyme is nitroreductase gene. In one embodiment, the suicide enzyme is the *E. coli* gpt gene. In one embodiment, the suicide enzyme is *E. coli* Deo gene.

Delivery of Ablative Component

In one embodiment, the ablative component is delivered to cardiac tissue via direct injection into a coronary artery supplying the region of tissue where the ablation is desired. In one embodiment, the ablative component is delivered to cardiac tissue via direct injection into the cardiac muscle in the region of tissue where the ablation is desired. In one embodiment, the ablative component is delivered to cardiac tissue via injection into the pericardial space. In one embodiment, the ablative component is delivered to the cardiac tissue via retrograde injection into a coronary vein collecting blood from the general region of tissue where the ablation is desired. In one embodiment, the ablative component is delivered systemically by intravenous injection. In one embodiment, the ablative component is delivered systemically orally.

Delivery of Triggering Component

In one embodiment, the triggering component is delivered via a catheter directed to the tissue where ablation is desired. In one embodiment, the triggering component is light comprised of one or more spectral frequencies.

Optical Ablation Device

An optical ablation system delivers an ablation light to the site of ablation using an optical ablation catheter. The ablation light has characteristics including a wavelength suitable for optical ablation as discussed in this document. The optical ablation catheter is a long, thin flexible tube that delivers the light. The ablation site includes a specific location inside a body cavity (e.g., a heart chamber). This is done to activate a molecular ablation system for the treatment of abnormal heart beats (cardiac arrhythmias) due to the loss of the normal rhythm of the heart.

The optical ablation catheter may be placed into a vein near the groin at the top of the leg (femoral vein). It is then threaded through the vein into the chambers of the heart. The end of the catheter outside the body is connected to an electrical system that allows the physician to view the beating heart on a screen. By watching the screen, the physician can place the catheter in the correct spot to treat the abnormal heart beats. Once the catheter is in place, the physician turns on a light generator to emit light from the tip of the catheter. The light activates a light responsive promoter and/or releases a drug from a photosensitive cage. The activated gene expression inhibits impulse conduction or destroys heart tissue in a small area of the heart that causes the abnormal heart beat. This destruction of tissue is called "ablation."

In one application, the optical ablation system is used to treat patients who have atrial flutter, which is a form of tachycardia occurring in the atria. The destruction of a small amount of heart tissue resulting from an ablation blocks the abnormal impulse conduction pathways in the heart that cause atrial flutter.

FIG. 1 is an illustration of an embodiment of such an optical ablation system 100. Optical ablation system 100 includes an optical ablation catheter 102 and an external system 120. Optical ablation catheter 102 has a proximal end 103 to be connected to external system 120, a distal end 104 to be placed on or near the ablation site, and an elongate catheter body 105 coupled between proximal end 103 and distal end 104.

Optical ablation catheter 102 includes an optical ablation device 111, which includes a light emission device 108, a light connector 110, and a light link 109. Light emission device 108 is at distal end 104 and emits an ablation light, which is a light having characteristics selected to regulate an optically regulatable transcription control element operably linked to a nucleic acid sequence for a gene product, the expression of which gene product in cells directly or indirectly kills cells. In one embodiment, the wavelength of the ablation light is from 300 to 1000 nanometers (nm) or 350 to 500 nm, with approximately 450 nm being a specific example. In one embodiment, the intensity of the ablation light is from 150 to 15,000 micromol photons/m$^2$, with approximately 600 micromol photons/m$^2$ being a specific example. In one embodiment, light emission device 108 includes an optical filter to produce the ablation light by allowing passage of light having a specified range of wavelengths. Light connector 110 allows for connection between optical ablation device 111 and external system 120. Light link 109 extends within elongate body 105 and connects light emission device 108 to light connector 110. In one embodiment, light emission device 108 includes one or more light emitting diodes (LEDs) that emit the ablation light. Light link 109 includes electrical conductors. Light connector 110 provides an electrical connection between an electrical power source in external system 120 and the one or more LEDs via the electrical conductors. In another embodiment, light emission device 108 includes the distal terminal of a fiber optic cable that transmits the ablation light generated from a light source in external system 120. Light link 109 includes the fiber optic cable. Light connector 110 provides for an optical connection to a light source in external system 120 and the terminal of the fiber optic cable at proximal end 103.

In the illustrated embodiment, optical ablation catheter 102 includes a projection control mechanism 112 in addition to an optical ablation device 111. Projection control mechanism 112 is coupled to light emission device 108 and controls an effectively illuminated area, which is an area where the optically regulatable transcription control element is effectively regulatable by the ablation light projected from light emission device 108. In the illustrated embodiment, projection control mechanism 112 is an adjustable projection control mechanism that allows adjustable control of the effectively illuminated area and includes a distal projection control device 113, a proximal projection control device 115, and a projection control link 114. Distal projection control device 113 is coupled to light emission device 108 at distal end 104 and determines the effectively illuminated area. Proximal projection control device 115 allows control of the effectively illuminated area by adjusting distal projection control device 113 from proximal end 103. Projection control link 114 extends within elongate catheter body 105 and coupled between distal projection control device 113 and proximal projection control device 115. In other embodiments, projection control mechanism 112 is a fixed projection control mechanism that includes distal projection control device 113 that determines the effectively illuminated area.

Figure 2:
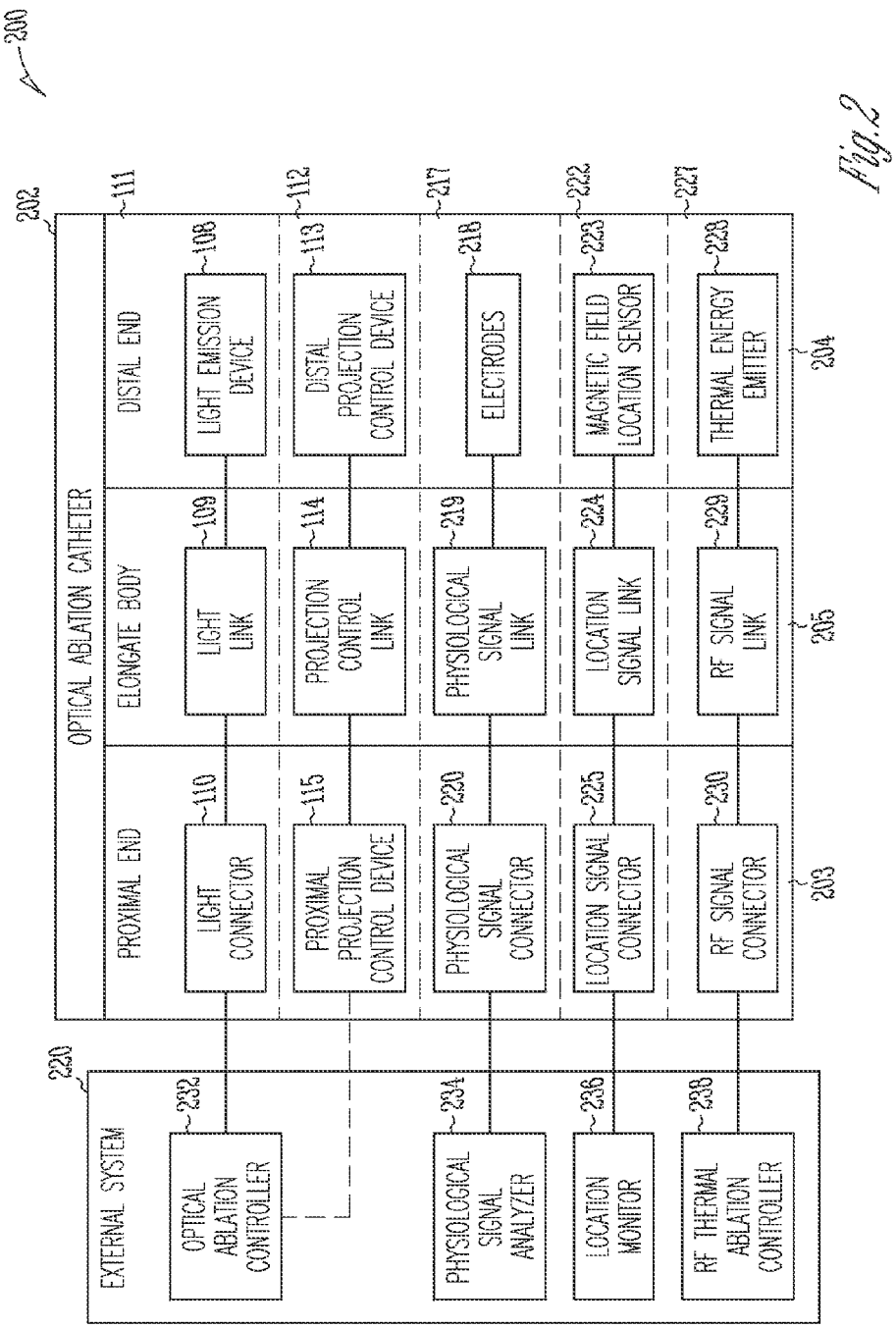
FIG. 2 is a block diagram illustrating an embodiment of the optical ablation system.

FIG. 2 is a block diagram illustrating an embodiment of an optical ablation system 200, which represents a specific embodiment of optical ablation system 100. Optical ablation system 200 includes an optical ablation catheter 202 and an external system 220. Optical ablation catheter 202 represents a specific embodiment of optical ablation catheter 102 and includes a proximal end 203, a distal end 204, and an elongate catheter body 205 coupled between proximal end 203 and distal end 204. External system 220 represents a specific embodiment of external system 120. In the illustrated embodiment, optical ablation catheter 202 includes optical ablation device 111, a projection control mechanism 112, a physiological sensing device 217, a location device 222, and a radio-frequency (RF) ablation device 227. External system 220 includes an optical ablation controller 232, a physiological signal analyzer 234, a location monitor 236, and an RF thermal ablation controller 238. In various embodiments, in addition to optical ablation device 111 and projection control mechanism 112, optical ablation catheter 202 includes any one or more of physiological sensing device 217, location device 222, and radio-frequency (RF) ablation device 227. In addition to optical ablation controller 232, external device 220 includes the corresponding one or more of physiological signal analyzer 234, location monitor 236, and RF thermal ablation controller 238.

Optical ablation device 111 includes light emission device 108 at distal end 204, light connector 110 at proximal end 203, a light link 109 extending within elongate catheter body 205. Projection control mechanism 112 includes distal projection control device 113 at distal end 204, proximal projection control device 115 at proximal end 203, and projection control link 114 extending within elongate catheter body 205. Various examples of projection control mechanism 112 are discussed below with references to FIGS. 3-8. Optical ablation controller 232 generates electrical and/or optical signals and controls the timing and intensity of the ablation light emitted from light emission device 108.

Physiological sensing device 217 allows for physiological signal sensing and includes electrodes 218, a physiological signal connector 220, and a physiological signal link 219. Electrodes 218 are at and/or near distal end 204 for sensing one or more physiological signals. Physiological signal connector 220 is at proximal end 203 and provides for connection between physiological sensing device 217 and physiological signal analyzer 234. Physiological signal link 219 extends within elongate catheter body 205 and includes electrical conductors that provide for electrical connections between electrodes 218 and physiological signal connector 220. In one embodiment, physiological sensing device 217 allows sensing of one or more intracardiac electrograms, and physiological signal analyzer 234 maps electrical activities on heart 101 (FIG. 1) using the sensed one or more intracardiac electrograms.

Location device 222 allows for monitoring of location of distal end 204 and includes a magnetic field location sensor 223, a location signal connector 225, and a location signal link 224. Magnetic field location sensor 223 is at the distal end 204 and senses a signal indicative of the location of distal end 204. Location signal connector 225 is at proximal end 203 and provides for connection between location device 222 and location monitor 236. Location signal link 224 extends within elongate catheter body 205 and provides for connection between magnetic field location sensor 223 and location signal connector 225. Location monitor 236 allows a user to monitor the location of distal end 204 in a body after it has entered the body. One example of a system including location device 222 and location monitor 236 is the CARTO® electroanatomical mapping system (Biosense Webster, Inc., Diamond Bar, Calif.).

RF ablation device 227 provides RF thermal ablation as an alternative or supplement to the optical ablation and includes a thermal energy emitter 228, an RF signal connector 230, and an RF signal link 229. Thermal energy emitter 228 is at distal end 204 and generates a thermal energy suitable for thermal ablation using an RF signal. RF signal connector 230 is at proximal end 203 and provides for connection between RF ablation device 227 and RF thermal ablation controller 238. RF signal link 229 extends within elongate catheter body 205 and includes electrical conductors that provide for connection between thermal energy emitter 228 and RF signal connector 238. RF thermal ablation controller 238 includes an RF signal generator and controls the timing and amplitude of the thermal energy emitted from thermal energy emitter 228. In various embodiments, optical ablation catheter 202 includes one or more other (non-optical) ablation devices. Such ablation devices are used when the optical ablation is ineffective or inappropriate. In addition to the RF thermal ablation, another example of such an ablation device is an cryoablation device.

Figure 6:
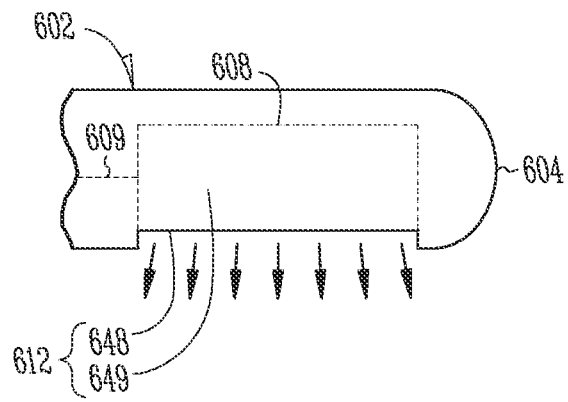
FIG. 6 is an illustration of another embodiment of a distal portion of the optical ablation catheter.
Figure 7:
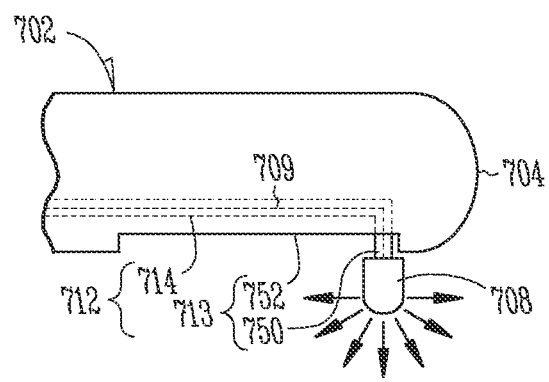
FIG. 7 is an illustration of another embodiment of a distal portion of the optical ablation catheter.
Figure 8:
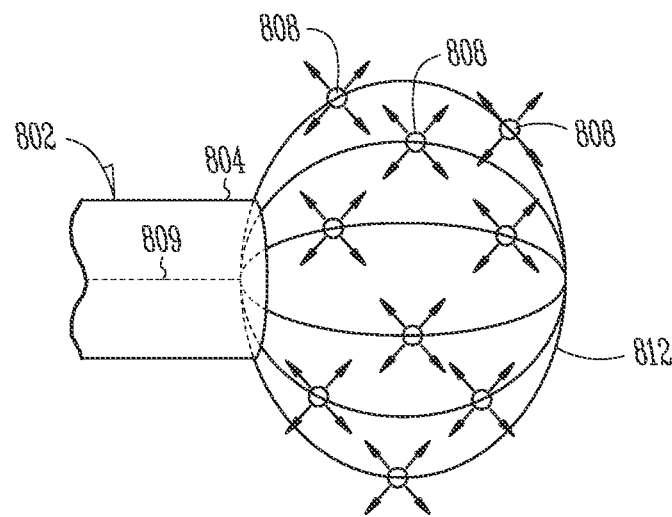
FIG. 8 is an illustration of another embodiment of a distal portion of the optical ablation catheter.

FIGS. 3-8 illustrate, by way of example, various embodiments of projection control mechanism 112. In various embodiments, a projection control mechanism provides adjustable control of the effectively illuminated area, such as illustrated in FIGS. 3, 4, 5, and 7. In various other embodiments, a projection control mechanism provides fixed control of the effectively illuminated area, such as illustrated in FIGS. 6 and 8. In FIGS. 3-8, optical ablation catheters 302, 402, 502, 602, 702, and 802 each represent a specific embodiment of optical ablation catheters 102 or 202, with distal ends 304, 404, 504, 604, 704, and 804 corresponding to distal end 104 or 204. Light mission devices 308, 408, 508, 608, 708, and 808 each represent a specific embodiment of light emission device 108. While having various shapes, these light emission devices each emit the ablation light for performing the optical ablation as discussed in this document. Light link 309, 409, 509, 609, 709, and 809 each represent a specific embodiment of light link 109 and include electrical conductors and/or one or more fiber optic cables. Projection control mechanism 312, 412, 512, 612, 712, and 812 each represent a specific embodiment of projection control mechanism 112. Distal projection control device 313, 413, 513, 713, and each represent a specific embodiment of distal projection control device 113 and determine the effectively illuminated area. Projection control link 314, 414, 514, and 714 each represent a specific embodiment of projection control link 114 and allow for control of the corresponding distal projection control device from the proximal end of the optical ablation cable.

FIG. 3A is a side view, and FIG. 3B is a front view, that illustrate an embodiment of a distal portion, including distal end 304, of optical ablation catheter 302, which includes adjustable projection control mechanism 312. Distal projection control device 313 of adjustable projection control mechanism 312 includes a diaphragm in the light emission path of light emission device 308 to control the projection of the ablation light. The diaphragm includes an adjustable aperture 341 to limit the amount of the ablation light projected to the ablation site. In the illustrated embodiment, the diaphragm is an iris diaphragm having overlapping plates folding in each other. Projection control link 314 allows for adjustment of aperture 341 from the proximal end of optical ablation catheter 302.

FIG. 4 is an illustration of an embodiment of a distal portion, including distal end 404, of optical ablation catheter 402, which includes adjustable projection control mechanism 412. Light emission device 408 is an elongate light emission device. In one embodiment, light emission device 408 has an elongate cylindrical shape. Distal projection control device 413 of adjustable projection control mechanism 412 includes a retractable non-transparent sleeve that surrounds at least a portion of elongate light emission device 408. The sleeve slides over elongate light emission device 408 along the longitudinal axis of optical ablation catheter 402 to determine the amount of exposure of elongate light emission device 408 and hence the amount of the ablation light projected to the ablation site. To increase the amount of the ablation light projected to the ablation site, the sleeve retracts into distal end 404. Projection control link 414 allows for positioning of the sleeve relative to elongate light emission device 408 from the proximal end of optical ablation catheter 402.

FIG. 5 is an illustration of an embodiment of a distal portion, including distal end 504, of optical ablation catheter 502, which includes adjustable projection control mechanism 512. Adjustable projection control mechanism 512 is similar to adjustable projection control mechanism 412 except that it includes a transparent bubble 545 coupled to distal end 504. Light emission device 508 is an elongate light emission device. In one embodiment, light emission device 508 has an elongate cylindrical shape. Distal projection control device 513 of adjustable projection control mechanism 512 includes a retractable non-transparent sleeve 543 that surrounds at least a portion of elongate light emission device 508. Sleeve 543 slides over elongate light emission device 508 along the longitudinal axis of optical ablation catheter 502 to determine the amount of exposure of elongate light emission device 508 and hence the amount of the ablation light projected to the ablation site. To increase the amount of the ablation light projected to the ablation site, sleeve 543 retracts into distal end 504. Projection control link 514 allows for positioning of sleeve 543 relative to elongate light emission device 508 from the proximal end of optical ablation catheter 502. In the illustrated embodiment, a non-transparent tip 546 is attached to the distal end of light emission device 508 to allow performance of circular ablation. That is, optical ablation catheter 502 projects light from distal end 504 in directions perpendicular to its the longitudinal axis when bubble 545 is wedged into a blood vessel 501. For example, bubble 545 may be configured to fit into the pulmonary vein ostia for pulmonary vein antrum isolation (PVAI). During PVAI, optical ablation catheter 502 is inserted into the blood vessels of an atrium. The optical ablation is performed to form a circular scar that blocks impulses firing from within the pulmonary vein to "disconnect" the pathway of abnormal rhythm and prevent AF. In one embodiment, bubble 545 is expandable and contractible. For example, after being deployed in a vessel, bubble 545 is inflated for the optical ablation. After the optical ablation is completed, bubble 545 is deflated for easy removal of catheter 502 from the body.

FIG. 6 is an illustration of an embodiment of a distal portion, including distal end 604, of optical ablation catheter 602, which includes projection control mechanism 612. Light emission device 608 is an elongate light emission device. In one embodiment, light emission device 608 has an elongate cylindrical shape. Projection control mechanism 612 includes a distal projection control device including a non-transparent shield 649 over elongate light emission device 608 and a slit 648 on non-transparent shield 649. The ablation light is projected from light emission device 608 through slit 648. In one embodiment, the ablation is to be performed along a "cutting line" on the tissue at the ablation site, and slit 648 is positioned over the intended cutting line. In one embodiment, the distal portion of optical ablation catheter 602 including slit 648 has an approximately circular shape, or otherwise a curved shape allowing alignment of slit 648 with a region to be ablated, such as the pulmonary vein ostia. In one embodiment, the distal portion of optical ablation catheter 602 is configured to be an approximately circular loop having a diameter between 15 and 30 millimeters. Slit 648 is formed along the entire length of the loop. In one embodiment, the distal portion of optical ablation catheter 602 (the circular loop) has a 7 French diameter. Slit 648 includes about one third of the surface area of the circular loop and is positioned to be facing the region to be ablated after deployment of the catheter another embodiment, the entire the circular loop is made transparent.

FIG. 7 is an illustration of an embodiment of a distal portion, including distal end 704, of optical ablation catheter 702, which includes adjustable projection control mechanism 712. Distal projection control device 713 of adjustable projection control mechanism 712 includes a light positioning device 750 and a slot 752 on the body of optical ablation catheter 702 at and/or near distal end 704. Light emission device 708 is connected to light positioning device 750. Slot 752 allows light positioning device 750, and hence light emission device 708, to be slid along the longitudinal axis of optical ablation catheter 702. Projection control link 714 is connected to light positioning device 750 and allows for the positioning of light emission device 708 from the proximal end of optical ablation catheter 702.

FIG. 8 is an illustration of an embodiment of a distal portion, including distal portion 804, of optical ablation catheter 802, which includes projection control mechanism 812. Projection control mechanism 812 includes a distal projection control device including a mesh balloon. Light emission device 808 includes a plurality of light emission devices distributed over the mesh balloon. In various embodiments, the plurality of light emission devices includes a plurality of LEDs or a plurality of fiber optic terminals branching from one or more fiber optic cables of light link 809.

Gene Therapy Vectors

Gene therapy vectors include, for example, viral vectors, liposomes and other lipid-containing complexes, and other macromolecular complexes capable of mediating delivery of a gene to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector by the cell; components that influence localization of the transferred gene within the cell after uptake (such as agents mediating nuclear localization); and components that influence expression of the gene. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., WO 92/08796; and WO 94/28143). Such marker genes can provide an added measure of control that can be advantageous in gene therapy contexts. A large variety of such vectors are known in the art and are generally available.

Gene therapy vectors within the scope of the invention include, but are not limited to, isolated nucleic acid, e.g., plasmid-based vectors which may be extrachromosomally maintained, and viral vectors, e.g., recombinant adenovirus, retrovirus, lentivirus, herpesvirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes. Exemplary gene therapy vectors are described below. Gene therapy vectors may be administered via any route including, but not limited to, intramuscular, buccal, rectal, intravenous or intracoronary administration, and transfer to cells may be enhanced using electroporation and/or iontophoresis.

Retroviral Vectors

Retroviral vectors exhibit several distinctive features including their ability to stably and precisely integrate into the host genome providing long-term transgene expression. These vectors can be manipulated ex vivo to eliminate infectious gene particles to minimize the risk of systemic infection and patient-to-patient transmission. Pseudotyped retroviral vectors can alter host cell tropism.

Lentiviruses

Lentiviruses are derived from a family of retroviruses that include human immunodeficiency virus and feline immunodeficiency virus. However, unlike retroviruses that only infect dividing cells, lentiviruses can infect both dividing and nondividing cells. For instance, lentiviral vectors based on human immunodeficiency virus genome are capable of efficient transduction of cardiac myocytes in vivo. Although lentiviruses have specific tropisms, pseudotyping the viral envelope with vesicular stomatitis virus yields virus with a broader range (Schnepp et al., *Meth. Mol. Med.,* 69:427 (2002)).

Adenoviral Vectors

Adenoviral vectors may be rendered replication-incompetent by deleting the early (E1A and E1B) genes responsible for viral gene expression from the genome and are stably maintained into the host cells in an extrachromosomal form. These vectors have the ability to transfect both replicating and nonreplicating cells and, in particular, these vectors have been shown to efficiently infect cardiac myocytes in vivo, e.g., after direction injection or perfusion. Adenoviral vectors have been shown to result in transient expression of therapeutic genes in vivo, peaking at 7 days and lasting approximately 4 weeks. The duration of transgene expression may be improved in systems utilizing cardiac specific promoters. In addition, adenoviral vectors can be produced at very high titers, allowing efficient gene transfer with small volumes of virus.

Adeno-Associated Virus Vectors

Recombinant adeno-associated viruses (rAAV) are derived from nonpathogenic parvoviruses, evoke essentially no cellular immune response, and produce transgene expression lasting months in most systems. Moreover, like adenovirus, adeno-associated virus vectors also have the capability to infect replicating and nonreplicating cells and are believed to be nonpathogenic to humans. Moreover, they appear promising for sustained cardiac gene transfer (Hoshijima et al., *Nat. Med.,* 8:864 (2002); Lynch et al., *Circ. Res.,* 80:197 (1997)).

Herpes Virus/Amplicon

Herpes simplex virus 1 (HSV-1) has a number of important characteristics that make it an important gene delivery vector in vivo. There are two types of HSV-1-based vectors: 1) those produced by inserting the exogenous genes into a backbone virus genome, and 2) HSV amplicon virions that are produced by inserting the exogenous gene into an amplicon plasmid that is subsequently replicated and then packaged into virion particles. HSV-1 can infect a wide variety of cells, both dividing and nondividing, but has obviously strong tropism towards nerve cells. It has a very large genome size and can accommodate very large transgenes (>35 kb). Herpesvirus vectors are particularly useful for delivery of large genes, e.g., genes encoding ryanodine receptors and titin.

Plasmid DNA Vectors

Plasmid DNA is often referred to as "naked DNA" to indicate the absence of a more elaborate packaging system. Direct injection of plasmid DNA to myocardial cells in vivo has been accomplished. Plasmid-based vectors are relatively nonimmunogenic and nonpathogenic, with the potential to stably integrate in the cellular genome, resulting in long-term gene expression in postmitotic cells in vivo. For example, expression of secreted angiogenesis factors after muscle injection of plasmid DNA, despite relatively low levels of focal transgene expression, has demonstrated significant biologic effects in animal models and appears promising clinically (Isner, *Nature,* 415:234 (2002)). Furthermore, plasmid DNA is rapidly degraded in the blood stream; therefore, the chance of transgene expression in distant organ systems is negligible. Plasmid DNA may be delivered to cells as part of a macromolecular complex, e.g., a liposome or DNA-protein complex, and delivery may be enhanced using techniques including electroporation.

Synthetic Oligonucleotides

Antisense oligonucleotides are short (approximately 10 to 30 nucleotides in length), chemically synthesized DNA molecules that are designed to be complementary to the coding sequence of an RNA of interest. These agents may enter cells by diffusion or liposome-mediated transfer and possess relatively high transduction efficiency. These agents are useful to reduce or ablate the expression of a targeted gene while unmodified oligonucleotides have a short half-life in vivo, modified bases, sugars or phosphate groups can increase the half-life of oligonucleotide. For unmodified nucleotides, the efficacy of using such sequences is increased by linking the antisense segment with a specific promoter of interest, e.g., in an adenoviral construct. In one embodiment, electroporation and/or liposomes are employed to deliver plasmid vectors. Synthetic oligonucleotides may be delivered to cells as part of a macromolecular complex, e.g., a liposome, and delivery may be enhanced using techniques such as electroporation.

Regulatable Transcription Control Elements

The device of the invention may deliver one or more signals including, but not limited to, light of a particular wavelength or a range of wavelengths, light of a particular energy, acoustic energy, an electric field, a chemical, electromagnetic energy, thermal energy or other forms of temperature or matter, which signal is recognized by a regulatable transcription control element in a gene therapy vector.

A variety of strategies have been devised to control in vivo expression of transferred genes and thus alter the pharmacokinetics of in vivo gene transfer vectors in the context of regulatable or inducible promoters. Many of these regulatable promoters use exogenously administered agents to control transgene expression and some use the physiologic milieu to control gene expression. Examples of the exogenous control promoters include the tetracycline-responsive promoter, a chimeric transactivator consisting of the DNA and tetracycline-binding domains from the bacterial tet repressor fused to the transactivation domain of herpes simplex virion protein 16 (Ho et al., *Brain Res. Mol. Brain. Res.,* 41:200 (1996)); a chimeric promoter with multiple cyclic adenosine monophosphate response elements superimposed on a minimal fragment of the 5'-flanking region of the cystic fibrosis transmembrane conductance regulator gene (Suzuki et al., 7:1883 (1996)); the EGR1 radiation-inducible promoter (Hallahan et al., *Nat. Med.,* 1:786 (1995)); and the chimeric GRE promoter (Lee et al., *J. Thoracic Cardio. Surg.,* 118:26 (1996)), with 5 GREs from the rat tyrosine aminotransferase gene in tandem with the insertion of Ad2 major late promoter TATA box-initiation site (Narumi et al., *Blood,* 92:812 (1998)). Examples of the physiologic control of promoters include a chimera of the thymidine kinase promoter and the thyroid hormone and retinoic acid-responsive element responsive to both exogenous and endogenous tri-iodothyronine (Hayashi et al., *J. Biol. Chem.,* 269:23872 (1994)); complement factor 3 and serum amyloid A3 promoters responsive to inflammatory stimuli; the grp78 and BiP stress-inducible promoter, a glucose-regulated protein that is inducible through glucose deprivation, chronic anoxia, and acidic pH (Gazit et al., *Cancer Res.,* 55:1660 (1995)); and hypoxia-inducible factor 1 and a heterodimeric basic helix-loop-helix protein that activates transcription of the human erythropoietin gene in hypoxic cells, which has been shown to act as a regulatable promoter in the context of gene therapy in vivo (Forsythe et al., *Mol. Cell. Biol.,* 16:4604 (1996)).

Regulatable transcription elements useful in gene therapy vectors and methods of the invention include, but are not limited to, a truncated ligand binding domain of a progestin receptor (controlled by antiprogestin), a tet promoter (controlled by tet and dox) (Dhawan et al., *Somat. Cell. Mol. Genet.,* 21, 233 (1995); Gossen et al., *Science,* 268:1766 (1995); Gossen et al., *Science,* 89:5547 (1992); Shockett et al., *Proc. Natl. Acad. Sci. USA,* 92, 6522 (1995)), hypoxia-inducible nuclear factors (Semenza et al., *Proc. Natl. Acad. Sci. USA,* 88, 5680 (1991); Semenza et al., *J. Biol. Chem.,* 269, 23757)), steroid-inducible elements and promoters, such as the glucocorticoid response element (GRE) (Mader and White, *Proc. Natl. Acad. Sci. USA,* 90, 5603 (1993)), and the fusion consensus element for RU486 induction (Wang et al., *Proc. Natl. Acad. Sci. USA,* 91:818 (1994)), those sensitive to electromagnetic fields, e.g., those present in metallothionine I or II, c-myc, and HSP70 promoters (Lin et al., *J. Cell. Biochem.,* 81:143 (2001); Lin et al., *J. Cell. Biochem.,* 54:281 (1994); U.S. published application 20020099026)), and electric pulses (Rubenstrunk et al., *J. Gene Med.,* 5:773 (2003)), as well as a yeast GAL4/TATA promoter, auxin inducible element, an ecdysone responsive element (No et al., *Proc. Natl. Acad. Sci. USA,* 93:3346 (1996)), an element inducible by rapamycin (FK506) or an analog thereof (Rivera et al., *Nat. Med.,* 2:1028 (1996); Ye et al., *Science,* 283:88 (1999); Rivera et al., *Proc. Natl. Acad. Sci. USA,* 96:8657 (1999)), a tat responsive element, a metal, e.g., zinc, inducible element, a radiation inducible element, e.g., ionizing radiation has been used as the inducer of the promoter of the early growth response gene (Erg-1) (Hallahan et al., *Nat. Med.,* 1:786 (1995)), an element which binds nuclear receptor PPARγ (peroxisome proliferators activated receptors), which is composed of a minimal promoter fused to PPRE (PPAR responsive elements, see WO 00/78986), a cytochrome P450/A1 promoter, a MDR-1 promoter, a promoter induced by specific cytokines (Varley et al., *Nat. Biotech.,* 15:1002 (1997)), a light inducible element (Shimizu-Sato et al., *Nat. Biotech.,* 20:1041 (2002)), a lacZ promoter, and a yeast Leu3 promoter. In one embodiment, the regulatable transcription control element is regulated by light. Promoters or other transcription control elements regulated by light include but are not limited to those disclosed in U.S. Pat. Nos. 6,858,429 (red or far-red light; 600 nm-750 nm), and 6,733,996 (430 nm to 480 nm). Thus, the methods and systems of the invention may include the use of other expression cassettes to express heterologous gene products that confer light responsiveness. For example, the other expression cassettes may encode WC1 and WC2 or a light responsive protein that binds to a promoter, or a fusion protein having a transcription factor binding protein fused to a light sensitive protein.

In one embodiment, the regulatable transcription control element is regulated by light. Light regulated genes include but are not limited to phytolyases, phytochromes, white collar complex (WCC), cryptochromes, phototropins, mimecan, chalcone synthases (CHS), encephalopsin, photoactive yellow protein, and dark stripe.

CPD photolyases repair cyclobutane pyrimidine dimers (CPDs) induced in DNA. Photolyases are found in many organisms including but not limited to *E. coli, A. nidulans, P. tridactylus, D. melanogaster, O. latipes, C. auratus, M. domestica, T. harzianum,* and *S. cerevisiae.* Photolyases contain one flavin adenine dinucleotide (FAD) and either a methenyltetrahydrofolate (MTHF, type-1 photolyases) or an 8-hydroxy-5-deazariboflavin (type-2 photolyases). The photolyase binds the DNA dimer and the coenzyme receives blue light (350 to 500 nm). The induction of the photolyase gene is very rapid (about 15 to 30 minutes) and significant. The system may be altered by substituting flavins responsive to other wavelengths of light.

Phytochromes are protein complexes composed of bilin chromophores. The bilin chromophore (light-sensing structure) is a linear tetrapyrrole (four 5-carbon rings covalently bonded) which is synthesized from heme by several enzymes. The apophytochrome protein spontaneously binds the chromophore in the cell cytoplasm to form the phytochrome complex. This is a covalent association via a thioether linkage. The phytochrome has 1-3 PAS domains involved in protein-protein interaction and nuclear localization, a GAF domain, and a PHY domain at the N-terminus and a histidine kinase-related domain (HKRD) at the C-terminus (Rockwell et al., 2006). When the phytochrome complex is exposed to seconds to minutes of red light of about 660 nm, the inactive form of the complex ($P_R$) undergoes isomerization to the active ($P_{FR}$) form. This exposes the nuclear localization signal in the PAS domain, allowing for nuclear localization where the N-terminal domains interact with transcription factors. When the $P_{FR}$ phytochrome complex is exposed to seconds to minutes of far red light of about 750 nm, it converts back to the $P_R$ form and leaves the nucleus, stopping gene regulation. Alternately, if the $P_{FR}$ phytochrome complex is left with no light stimulation for several hours it will revert to the $P_R$ form. Phytochrome complexes can be found in all flowering plants and cryptophytes, cyanobacteria, nonoxygenic bacteria, and fungi. A tyrosine-to-histidine mutation of the phytochrome causes it to give off an intense red fluorescence when excited by light.

For instance, U.S. Pat. No. 6,887,688 discloses a cell with hemeoxygenase and a ferredoxin-dependent bilin reductase (such as PcyA or HY2) to produce the bilin component of the phytochrome complex, a gene for the C-terminal PAS domain of the phytochrome (which functions as an nuclear localization signal (NLS)) genetically combined with an N-terminal transcription factor of choice, and a target gene with a promoter which corresponds to the transcription factor.

U.S. patent application No. 2003/0082809A1 discloses a cell with a phytochrome genetically engineered with a DNA-binding domain (DBD, constitutively expressed, a chromophore (expressed or added exogenously), a phytochrome interacting factor (PIF) genetically engineered with an activating domain (AD, constitutively expressed), and a target gene with a promoter which corresponds to the activating domain. The phytochrome-DBD binds to the target gene and in the presence of red light it interacts with the PIF-AD to initiate transcription of the target gene. It ceases to interact with the PIF-AD in the presence of far red light, stopping transcription of the target gene.

The white collar-1 (WC-1) and white collar-2 (WC-2) proteins are transcriptional regulators. They bind promoters through GATA-type zinc-finger DNA binding-domains, and they complex with one another through PAS domains. One PAS domain on WC-1 is a member of the light, oxygen, or voltage (LOV) class, and is responsible for binding to flavin adenine dinucleotide (FAD). FAD serves as the blue light sensor for the white collar complex with peak responsiveness at 370 and 450 nm.

U.S. Pat. No. 6,733,996 describes a method for using the WCC to regulate gene expression. This invention involves a cell containing FAD (all cells have FAD) engineered with the WC-1 and WC-2 genes genetically linked to be expressed as a fusion protein in which the zinc-finger DBD of WC-1 is replaced with a different transactivator, and a target gene linked to a promoter element which corresponds to the transactivator.

Cryptochromes serve as blue light photoreceptors in both prokaryotes and eukaryotes. The cryptochrome (cry 1 and 2) have C-terminal extensions not found in photolyases. These C-terminal domains mediate a constitutive light response. It is hypothesized that these domains are in an inactive state in the dark and blue light relieves the repression through an intra- or intermolecular redox reaction with the flavin chromophore. Cry 1 binds to FAD, which may serve as its chromophore. Cry 2 is strongly downregulated by blue light. Cry 1 and 2 are known to be involved in light sensing in the retina.

Phototropins are membrane-bound kinases in plants which contain LOV (light, oxygen, voltage) PAS domains and bind FMN (flavin mononucleotide) to sense blue light. Light appears to cause a conformational change in phototropins, exposing the PAS domains and activating kinase function, and allowing regulating of phototrophism in plants.

Promoters or other transcription control elements regulated by light useful in the compositions, methods, and systems of the invention include but are not limited to those disclosed in U.S. Pat. Nos. 6,858,429 (red or far-red light; 600 nm to 750 nm); 6,733,996 (430 nm to 480 nm); 6,887,688; a photolyase system which is chromophore-based system for DNA damage repair with a FAD cofactor, that is expressed rapidly after blue light exposure (350 nm to 500 nm); a phytochrome system which is a chromophore-based system that has a protein complex which interconverts in response to red and far red light (about 660 nm to about 750 nm); white collar complex, in which WC-1 and WC-2 bind FAD and regulate gene expression (450 nm to 470 nm); a cryptochrome system found in circadian clock mechanism and plant functions (broad UV-A band and blue light); a phototropin (nph1) system, where light activates protein kinase function; a human mimecan promoter, where encoded protein is induced about 24 hours after UV exposure; a CHS promoter, which is induced by UV light; an encephalopsin system; a photoactive yellow protein (maximum at 446 nm); and a dark-stipe1 (dst1) system (UV and blue light). Thus, the methods and systems of the invention may include the use of other expression cassettes to express heterologous gene products that confer light responsiveness.

In one embodiment, a gene expression system that is to be used for the delivery of device-regulated light-inducible gene therapy is rapidly and significantly inducible by light, tightly regulated, has low/no basal expression, and/or shuts off in the absence of light rapidly. In one embodiment, the light regulated transcription control element binds Pfr when exposed to red light. Thus, cardiac cells may include expression cassettes for phytochrome apoprotein, e.g., PcyA or Hy2, and optionally other proteins found in the complex that binds the light regulated transcription control element, WC1 and WC2 or other light responsive protein that binds to a promoter, or a fusion protein having a transcription factor binding protein fused to a light sensitive protein.

In one embodiment, a device that emits light from 350 to 500 nm, or any one or band of wavelengths from 350 to 500 nm, may be employed with a photolyase responsive promoter. In one embodiment, a device that emits light from 630 to 690 nm, or any one or band of wavelengths from 630 to 690 nm, may be employed with a photochrome responsive promoter. In one embodiment, a device that emits light from 430 to 490 nm, or any one or band of wavelengths from 430 to 490 nm, may be employed with a WCC responsive promoter. In one embodiment, the WCC associated proteins may be altered so that they are responsive to different wavelengths of light, e.g., to red light (for instance, 600 to 700 nm) to avoid the DNA damage associated with shorter wavelengths of light or other wavelengths. In one embodiment, a device that emits a broad UV band or blue light may be employed with a cryptochrome responsive promoter. In one embodiment, a device that emits UV light may be employed with a mimican, CHS or dst1 responsive promoter. In one embodiment, a device that emits light from 420 to 450 nm, or any one or band of wavelengths from 420 to 450 nm, may be employed with a photoactive yellow protein responsive promoter. In one embodiment, the promoter is responsive to wavelengths other than those that cause DNA damage or are associated with heat generation.

In some embodiments, cell- or tissue-specific control elements, such as muscle-specific and inducible promoters, enhancers and the like, will be of particular use, e.g., in conjunction with regulatable transcription control elements. Such control elements include, but are not limited to, those derived from the actin and myosin gene families, such as from the myoD gene family (Weintraub et al., *Science,* 251, 761 (1991)); the myocyte-specific enhancer binding factor MEF-2 (Cserjesi and Olson, *Mol. Cell. Biol.,* 11, 4854 (1991)); control elements derived from the human skeletal actin gene (Muscat et al., *Mol. Cell. Bio.,* 7, 4089 (1987)) and the cardiac actin gene; muscle creatine kinase sequence elements (Johnson et al., *Mol. Cell. Biol.,* 9, 3393 (1989)) and the murine creatine kinase enhancer (mCK) element; control elements derived from the skeletal fast-twitch troponin C gene, the slow-twitch cardiac troponin C gene and the slow-twitch troponin I genes.

Cardiac cell restricted promoters include but are not limited to promoters from the following genes: a α-myosin heavy chain gene, e.g., a ventricular α-myosin heavy chain gene, β-myosin heavy chain gene, e.g., a ventricular β-myosin heavy chain gene, myosin light chain 2v gene, e.g., a ventricular myosin light chain 2 gene, myosin light chain 2a gene, e.g., a ventricular myosin light chain 2 gene, cardiomyocyte-restricted cardiac ankyrin repeat protein (CARP) gene, cardiac α-actin gene, cardiac m2 muscarinic acetylcholine gene, ANP gene, BNP gene, cardiac troponin C gene, cardiac troponin I gene, cardiac troponin T gene, cardiac sarcoplasmic reticulum Ca-ATPase gene, skeletal α-actin gene, as well as an artificial cardiac cell-specific promoter.

Further, chamber-specific promoters or enhancers may also be employed, e.g., for atrial-specific expression, the quail slow myosin chain type 3 (MyHC3) or ANP promoter, or the cGATA-6 enhancer, may be employed. For ventricle-specific expression, the iroquois homeobox gene may be employed. Examples of ventricular myocyte-specific promoters include a ventricular myosin light chain 2 promoter and a ventricular myosin heavy chain promoter.

In other embodiments, disease-specific control elements may be employed. Thus, control elements from genes associated with a particular disease, including but not limited to any of the genes disclosed herein may be employed in vectors of the invention.

Nevertheless, other promoters and/or enhancers which are not specific for cardiac cells or muscle cells, e.g., RSV promoter, may be employed in the expression cassettes and methods of the invention. Other sources for promoters and/or enhancers are promoters and enhancers from the Csx/NKX 2.5 gene, titin gene, α-actinin gene, myomesin gene, M protein gene, cardiac troponin T gene, RyR2 gene, Cx40 gene, and Cx43 gene, as well as genes which bind Mef2, dHAND, GATA, CarG, E-box, Csx/NKX 2.5, or TGF-beta, or a combination thereof.

The response of the regulatable transcriptional control element to one or more intermittent signals, a prolonged signal or different levels of a signal, may be tested in vitro or in vivo. The vector may include the regulatable transcriptional control element linked to a marker gene, i.e., one which is readily detectable or capable of detection such as green fluorescent protein (GFP). For example, a vector having a promoter which is sensitive to electrical pulses, a MT-I or MT-II promoter (Rubenstruck et al., *J. Gene Med.*, 5:773 (2003)), is linked to an open reading frame for a marker gene. The resulting expression cassette, e.g., one which is introduced to an adenovirus vector or to a plasmid vector, is employed to infect or transfect murine cells, e.g., murine cardiac cells, or heart sections. An electrode system designed for use in a small flask is used to deliver electrical pulses. Then fluorescence in the cells or a lysate thereof is detected, and/or or vector specific RNA is measured, for instance, using RT-PCR, and optionally compared to data from control cells. Similarly, a vector having a promoter which is sensitive to electrical pulses is linked to an open reading frame for a therapeutic gene, e.g., Serca2, introduced to cells, e.g., cardiac cells such as those with decreased levels of the gene product encoded by the therapeutic gene, and the phenotype of the recombinant cells compared to control cells. Vectors may also be introduced to a non-human large animal model, e.g., pigs, to determine the level and spatial expression of the exogenously introduced gene in response to signals, e.g., electrical pulses, from an implantable device in that animal.

Vector Delivery

Several techniques have been developed for cardiac gene delivery, including pericardial infusion, endomyocardial injection, intracoronary injection, coronary venous retroperfusion, and aortic root injection (Isner, *Nature*, 415:234 (2002)). The different techniques achieve variable response in homogeneity of gene delivery, resulting in focal gene expression within the heart (Hajjar et al., *Circ. Res.*, 86:616 (2000). For this reason, techniques that achieve diffuse uptake would seem to be superior. Two such methods utilize the heart's arterial and venous circulation to accomplish disseminated viral transfection. Arterial injection, performed directly through a percutaneous approach or indirectly by an infusion into the cross-clamped aorta, has shown promise in animal models of heart failure and is appealing in that it can be performed either at the time of cardiac surgery or as percutaneous intervention (Hajjar et al., *PNAS USA*, 95:5251 (1998)). Similarly, retroperfusion through the coronary sinus appears to produce a more global gene expression in comparison with techniques of localized or focal injection (Boeckstegers et al., *Circ.*, 100:1 (1999)).

The vector may be administered intravenously, transvenously, intramyocardially or by any other convenient route, and delivered by a needle, catheter, e.g., a catheter which includes an injection needle or infusion port, or other suitable device.

Direct Myocardial Injection

Direct myocardial injection of plasmid DNA as well as virus vectors, e.g., adenoviral vectors, and cells including recombinant cells has been documented in a number of in vivo studies. This technique when employed with plasmid DNA or adenoviral vectors has been shown to result in effective transduction of cardiac myocytes. Thus, direct injection may be employed as an adjunct therapy in patients undergoing open-heart surgery or as a stand-alone procedure via a modified thorascope through a small incision. Virus, e.g., pseudotyped, or DNA- or virus-liposome complexes may be delivered intramyocardially.

Catheter-Based Delivery

Intracoronary delivery of genetic material can result in transduction of approximately 30% of the myocytes predominantly in the distribution of the coronary artery. Parameters influencing the delivery of vectors via intracoronary perfusion and enhancing the proportion of myocardium transduced include a high coronary flow rate, longer exposure time, vector concentration, and temperature. Gene delivery to a substantially greater percent of the myocardium may be enhanced by administering the gene in a low-calcium, high-serotonin mixture (Donahue et al., *Nat. Med.*, 6:1395 (2000)). The potential use of this approach for gene therapy for heart failure may be increased by the use of specific proteins that enhance myocardial uptake of vectors (e.g., cardiac troponin T).

Improved methods of catheter-based gene delivery have been able to achieve almost complete transfection of the myocardium in vivo. Hajjar et al. (*Proc. Natl. Acad. Sci. USA*, 95:5251 (1998)) used a technique combining surgical catheter insertion through the left ventricular apex and across the aortic valve with perfusion of the gene of interest during cross-clamping of the aorta and pulmonary artery. This technique resulted in almost complete transduction of the heart and could serve as a protocol for the delivery of adjunctive gene therapy during open-heart surgery when the aorta can be cross-clamped.

Pericardial Delivery

Gene delivery to the ventricular myocardium by injection of genetic material into the pericardium has shown efficient gene delivery to the epicardial layers of the myocardium. However, hyaluronidase and collagenase may enhance transduction without any detrimental effects on ventricular function.

Intravenous Delivery

Intravenous gene delivery may be efficacious for myocardial gene delivery. However, to improve targeted delivery and transduction efficiency of intravenously administered vectors, targeted vectors may be employed. In one embodiment, intravenous administration of DNA-liposome or antibody-DNA complexes may be employed.

Lead-Based Delivery

Gene delivery can be performed by incorporating a gene delivery device or lumen into a lead such as a pacing lead, defibrillation lead, or pacing-defibrillation lead. An endocardial lead including a gene delivery device or lumen allows gene delivery to the endocardial layers of the myocardium. An epicardial lead including a gene delivery device or lumen allows gene delivery to the endocardial layers of the myocardium. A transvenous lead including a gene delivery device or lumen may also allow intravenous gene delivery. Lead-based delivery is particularly advantageous when the lead is used to deliver electrical and gene therapies to the same region.

Generally any route of administration may be employed, including oral, mucosal, intramuscular, buccal and rectal administration. For certain vectors, certain route of administration may be preferred. For instance, viruses, e.g., pseudotyped virus, and DNA- or virus-liposome, e.g., HVJ-liposome, may be administered by coronary infusion, while HVJ-liposome complexes may be delivered pericardially.

Dosages and Dosage Forms

The amount of gene therapy vector(s) administered and device based signal emitted to achieve a particular outcome will vary depending on various factors including, but not limited to, the gene and promoter chosen, the condition, patient specific parameters, e.g., height, weight and age, and whether prevention or treatment is to be achieved. The gene therapy vector/device system of the invention is amenable to chronic use for prophylactic purposes.

Vectors of the invention may conveniently be provided in the form of formulations suitable for administration, e.g., into the blood stream (e.g., in an intracoronary artery). A suitable administration format may best be determined by a medical practitioner for each patient individually, according to standard procedures. Suitable pharmaceutically acceptable carriers and their formulation are described in standard formulations treatises, e.g., Remington's Pharmaceuticals Sciences. Vectors of the present invention should preferably be formulated in solution at neutral pH, for example, about pH 6.5 to about pH 8.5, more preferably from about pH 7 to 8, with an excipient to bring the solution to about isotonicity, for example, 4.5% mannitol or 0.9% sodium chloride, pH buffered with art-known buffer solutions, such as sodium phosphate, that are generally regarded as safe, together with an accepted preservative such as metacresol 0.1% to 0.75%, more preferably from 0.15% to 0.4% metacresol. Obtaining a desired isotonicity can be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions. If desired, solutions of the above compositions can also be prepared to enhance shelf life and stability. Therapeutically useful compositions of the invention can be prepared by mixing the ingredients following generally accepted procedures. For example, the selected components can be mixed to produce a concentrated mixture which may then be adjusted to the final concentration and viscosity by the addition of water and/or a buffer to control pH or an additional solute to control tonicity.

The vectors can be provided in a dosage form containing an amount of a vector effective in one or multiple doses. For viral vectors, the effective dose may be in the range of at least about $10^7$ viral particles, preferably about $10^9$ viral particles, and more preferably about $10^{11}$ viral particles. The number of viral particles may, but preferably does not exceed $10^{14}$. As noted, the exact dose to be administered is determined by the attending clinician, but is preferably in 1 ml phosphate buffered saline. For delivery of plasmid DNA alone, or plasmid DNA in a complex with other macromolecules, the amount of DNA to be administered will be an amount which results in a beneficial effect to the recipient. For example, from 0.0001 to 1 mg or more, e.g., up to 1 g, in individual or divided doses, e.g., from 0.001 to 0.5 mg, or 0.01 to 0.1 mg, of DNA can be administered.

In one embodiment, in the case of heart disease, administration may be by intracoronary injection to one or both coronary arteries (or to one or more saphenous vein or internal mammary artery grafts or other conduits) using an appropriate coronary catheter. A variety of catheters and delivery routes can be used to achieve intracoronary delivery, as is known in the art. For example, a variety of general purpose catheters, as well as modified catheters, suitable for use in the present invention are available from commercial suppliers. Also, where delivery to the myocardium is achieved by injection directly into a coronary artery, a number of approaches can be used to introduce a catheter into the coronary artery, as is known in the art. By way of illustration, a catheter can be conveniently introduced into a femoral artery and threaded retrograde through the iliac artery and abdominal aorta and into a coronary artery. Alternatively, a catheter can be first introduced into a brachial or carotid artery and threaded retrograde to a coronary artery. Detailed descriptions of these and other techniques can be found in the art (see, e.g., above, including: Topol, (ed.), *The Textbook of Interventional Cardiology*, 4th Ed. (Elsevier 2002); Rutherford, *Vascular Surgery*, 5th Ed. (W.B. Saunders Co. 2000); Wyngaarden et al. (eds.), *The Cecil Textbook of Medicine*, 22nd Ed. (W.B. Saunders, 2001); and Sabiston, *The Textbook of Surgery*, 16th Ed. (Elsevier 2000)).

By way of illustration, liposomes and other lipid-containing gene delivery complexes can be used to deliver one or more transgenes. The principles of the preparation and use of such complexes for gene delivery have been described in the art (see, e.g., Ledley, *Human Gene Therapy*, 6:1129 (1995); Miller et al., *FASEB Journal*, 9:190 (1995); Chonn et al., *Curr. Opin. Biotech.*, 6:698 (1995); Schofield et al., *British Med. Bull.*, 51:56 (1995); Brigham et al., *J. Liposome Res.*, 3:31 (1993)).

Administration of the gene therapy vector in accordance with the present invention may be continuous or intermittent, depending, for example, upon the recipient's physiological condition, whether the purpose of the administration is therapeutic or prophylactic, and other factors known to skilled practitioners. The administration of the gene therapy vector may be essentially continuous over a preselected period of time or may be in a series of spaced doses. Both local and systemic administration is contemplated.

One or more suitable unit dosage forms comprising the gene therapy vector, which may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the vector with liquid carriers, solid matrices, semi-solid carriers, finely divided solid carriers or combinations thereof, and then, if necessary, introducing or shaping the product into the desired delivery system.

Pharmaceutical formulations containing the gene therapy vector can be prepared by procedures known in the art using well known and readily available ingredients. For example, the agent can be formulated with common excipients, diluents, or carriers, and formed into tablets, capsules, suspensions, powders, and the like. The vectors of the invention can also be formulated as elixirs or solutions for convenient oral administration or as solutions appropriate for parenteral administration, for instance by intramuscular, subcutaneous or intravenous routes.

The pharmaceutical formulations of the vectors can also take the form of an aqueous or anhydrous solution or dispersion, or alternatively the form of an emulsion or suspension.

Thus, the vector may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint.

For administration to the upper (nasal) or lower respiratory tract by inhalation, the vector is conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the vector may be administered via nose drops, a liquid spray, such as via a plastic bottle atomizer or metered-dose inhaler. Typical of atomizers are the Mistometer (Wintrop) and the Medihaler (Riker).

The local delivery of the vectors can also be by a variety of techniques which administer the vector at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

For topical administration, the vectors may be formulated as is known in the art for direct application to a target area. Conventional forms for this purpose include wound dressings, coated bandages or other polymer coverings, ointments, creams, lotions, pastes, jellies, sprays, and aerosols, as well as in toothpaste and mouthwash, or by other suitable forms. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-25% by weight.

When desired, the above-described formulations can be adapted to give sustained release of the active ingredient employed, e.g., by combination with certain hydrophilic polymer matrices, e.g., comprising natural gels, synthetic polymer gels or mixtures thereof.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The vector may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; mouthwashes comprising the composition of the present invention in a suitable liquid carrier; and pastes and gels, e.g., toothpastes or gels, comprising the composition of the invention.

The formulations and compositions described herein may also contain other ingredients such as antimicrobial agents or preservatives.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed:

1. An intravascular catheter for optical ablation of tissue in a living body having mammalian cells having an exogenously delivered optically regulatable transcription control element that is upregulated upon light emission and mammalian cells that lack the exogenously delivered optically regulatable transcription control element, the catheter comprising:
    a distal end;
    a proximal end;
    an elongate catheter body coupled between the distal end and the proximal end;
    a light emission device at the distal end and configured to emit light having characteristics including a wavelength and an intensity selected to ablate the mammalian cells having the exogenously delivered optically regulatable transcription control element that is upregulated upon near infrared light emission but not to ablate the mammalian cells that lack the exogenously delivered optically regulatable transcription control element, wherein the emitted light is near infrared light;
    a location device including a magnetic field location sensor at the distal end and configured to sense a location signal indicative of a location of the distal end;
    a projection control mechanism coupled to the light emission device and configured to project light that is perpendicular to the elongate catheter body where the optically regulatable transcription control element is effectively regulatable by the light projected from the light emission device; and
    a radio-frequency (RF) ablation device including a thermal energy emitter at the distal end and configured to generate a thermal energy suitable for ablating the tissue using an RF signal.

2. The catheter of claim 1 wherein the light emission device comprises one or more light emitting diodes (LEDs) configured to emit the light, and comprising electrical conductors extending within the elongate catheter body, and an electrical connector at the proximal end and connected to the one or more LEDs via the electrical conductors.

3. The catheter of claim 1 wherein the light emission device comprises a distal terminal of an fiber optic cable configured to transmit the light received at the proximal end, and comprising a fiber optic cable and an optical connector at the proximal end and connected to the fiber optic cable.

4. The catheter of claim 1 wherein the light emission device comprises an elongate light emission device, and the projection control mechanism comprises a non-transparent shield over the elongate light emission device and a slit on the shield, wherein the light is projected from the light projector through the slit.

5. The catheter of claim 1 wherein the light emission device comprises a plurality of light emission devices, and the projection control mechanism comprises a mesh balloon coupled to the distal end, and the light emission devices are distributed over the mesh.

6. The catheter of claim 1 wherein the projection control mechanism comprises an adjustable projection control mechanism configured to adjustably control the effectively illuminated area, the adjustable projection control mechanism including:
  a distal projection control device coupled to the light emission device;
  a proximal projection control device at the proximal end and configured to allow for control of the effectively illuminated area from the proximal end; and
  a projection control link extending within the elongate body and coupled between the distal projection control device and the proximal projection control device.

7. The catheter of claim 6 wherein the distal projection control device comprises a diaphragm coupled to the light emission device and configured to control the projection of the light, the diaphragm including an adjustable aperture configured to determine the amount of light projected from the light emission device.

8. The catheter of claim 6 wherein the light emission device comprises an elongate light emission device, the distal projection control device comprises a retractable non-transparent sleeve surrounding at least a portion of the elongate light emission device, the retractable non-transparent sleeve configured to slide over the elongate light emission device to determine the amount of the light projected from the elongate light emission device.

9. The catheter of claim 6 wherein the distal projection control device comprise a transparent bubble coupled to the distal end of the optical ablation catheter and a light positioning device connected to the light emission device, the light positioning device configured to allow the light emission device to be adjustably positioned in the transparent bubble.

10. The catheter of claim 9 wherein the bubble is expandable to fit the dimensions of a pulmonary vein ostia.

11. The catheter of claim 6 wherein the distal projection control device comprises a light positioning device configured to be slid along a portion of the optical ablation catheter, and the light emission device is attached onto the light positioning device.

12. The catheter of claim 6 further comprising a sensing device configured to allow for sensing of one or more physiological signals, the sensing device including one or more electrodes at the distal end.

13. An intravascular catheter for optical ablation of tissue in a living body having mammalian cells having an exogenously delivered optically regulatable transcription control element that is upregulated upon light emission and mammalian cells that lack the exogenously delivered optically regulatable transcription control element, the catheter comprising:
  a distal end;
  a proximal end;
  an elongate catheter body coupled between the distal end and the proximal end;
  a light emission device at the distal end and configured to emit light having characteristics including a wavelength and an intensity selected to ablate the mammalian cells having the exogenously delivered optically regulatable transcription control element that is upregulated upon light emission but not to ablate the mammalian cells that lack the exogenously delivered optically regulatable transcription control element;
  a physiological sensing device that includes electrodes, a physiological signal connector, and a physiological signal link, wherein the physiological signal connector provides for a connection between physiological sensing device and an external physiological signal analyzer; and
  a projection control mechanism coupled to the light emission device and configured to control an effectively illuminated area where the optically regulatable transcription control element is effectively regulatable by the light projected from the light emission device, wherein the projection control mechanism comprises an adjustable projection control mechanism configured to adjustably control the effectively illuminated area, the adjustable projection control mechanism including:
  a distal projection control device coupled to the light emission device, wherein the distal projection control device comprise a transparent bubble expandable to fit the dimensions of a pulmonary vein ostia coupled to the distal end of the optical ablation catheter and a light positioning device connected to the light emission device, the light positioning device configured to allow the light emission device to be adjustably positioned in the transparent bubble;
  a proximal projection control device at the proximal end and configured to allow for control of the effectively illuminated area from the proximal end; and
  a projection control link extending within the elongate body and coupled between the distal projection control device and the proximal projection control device.

* * * * *